United States Patent
Lynch et al.

(10) Patent No.: US 7,888,527 B2
(45) Date of Patent: Feb. 15, 2011

(54) ARYL AMIDE SPHINGOSINE 1-PHOSPHATE ANALOGS

(75) Inventors: Kevin R. Lynch, Charlottesville, VA (US); Timothy L. Macdonald, Charlottesville, VA (US); Jeremy J. Clemens, New City, NY (US); Michael D. Davis, Laurel, MD (US)

(73) Assignee: University of Virginia Patent Foundation, Charlottesville, VA (US)

( * ) Notice: Subject to any disclaimer, the term of this patent is extended or adjusted under 35 U.S.C. 154(b) by 630 days.

(21) Appl. No.: 11/720,998

(22) PCT Filed: Dec. 6, 2005

(86) PCT No.: PCT/US2005/044231

§ 371 (c)(1),
(2), (4) Date: Jun. 6, 2007

(87) PCT Pub. No.: WO2006/063033

PCT Pub. Date: Jun. 15, 2006

(65) Prior Publication Data

US 2009/0137531 A1 May 28, 2009

Related U.S. Application Data

(60) Provisional application No. 60/633,587, filed on Dec. 6, 2004.

(51) Int. Cl.
*C07F 9/22* (2006.01)

(52) U.S. Cl. .............................. 562/8; 562/15; 514/119

(58) Field of Classification Search ........................ None
See application file for complete search history.

(56) References Cited

U.S. PATENT DOCUMENTS

| | | | |
|---|---|---|---|
| 3,153,092 A | 10/1964 | Burger | |
| 5,773,475 A | 6/1998 | Kohn | |
| 2006/0046979 A1 | 3/2006 | Foster et al. | |
| 2006/0122181 A1 | 6/2006 | Ikemoto et al. | |
| 2006/0211656 A1 | 9/2006 | Albert et al. | |
| 2008/0249070 A1 | 10/2008 | Lynch et al. | |
| 2009/0042955 A1 | 2/2009 | Lynch et al. | |
| 2009/0062238 A1 | 3/2009 | Lynch et al. | |
| 2009/0105315 A1 | 4/2009 | Lynch et al. | |
| 2009/0253759 A1 | 10/2009 | Lynch et al. | |
| 2009/0253760 A1 | 10/2009 | Lynch et al. | |
| 2009/0253761 A1 | 10/2009 | Lynch et al. | |

FOREIGN PATENT DOCUMENTS

| | | |
|---|---|---|
| EP | 1 602 660 A1 | 12/2005 |
| JP | 1994 135935 | 5/1994 |
| JP | 1994 135936 | 5/1994 |
| JP | 2004 307442 | 4/2004 |
| WO | WO 2004010949 A2 * | 2/2004 |
| WO | WO 2004/047743 A2 | 6/2004 |
| WO | WO 2004/096757 A1 | 11/2004 |
| WO | WO 2005/118523 A1 | 12/2005 |
| WO | WO 2009/023854 A1 | 2/2009 |
| WO | WO 2009/043013 A2 | 4/2009 |
| WO | WO 2009/146112 A2 | 12/2009 |

OTHER PUBLICATIONS

Clemens, J. et al., *Bioorg. & Med. Chem. Lett.* (2004), 4903-4906.
Dworkin, R. H. et al., *Arch. Neurol.*, 60, 2003, p. 1524-1534.

\* cited by examiner

*Primary Examiner*—Sudhakar Katakam
(74) *Attorney, Agent, or Firm*—Rodney L. Sparks

(57) ABSTRACT

The present invention provides compounds that have antagonist activity at the $S1P_1$ and/or $S1P_3$ receptors. These compounds have enhanced selectivity and potency at the $S1P_1$ and/or $S1P_3$ receptors.

10 Claims, 12 Drawing Sheets

ARYL AMIDE SPHINGOSINE 1-PHOSPHATE ANALOGS

RELATED APPLICATIONS

This application is a national stage filing of International Application No. PCT/US2005/044231, filed on Dec. 6, 2005, which claims priority from a provisional application entitled: "META-SUBSTITUTED ARYL AMIDE SPHINGOSINE 1-PHOSPHATE ANALOGS AS S1P RECEPTOR ANTAGONISTS", filed on Dec. 6, 2004, Ser. No. 60/633,587, the entire disclosures of which are included herein by reference.

GOVERNMENT FUNDING

The invention described herein was made with government support under Grant Numbers GM067958 and GM064101, awarded by the National Institutes of Health. The United States Government has certain rights in the invention.

BACKGROUND OF THE INVENTION

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulator FTY720 (2-amino-2-[2-(4-octylphenyl)ethyl]propane-1,3-diol), that following phosphorylation, is a pan S1P receptor agonist, revealed that S1P tone influences lymphocyte trafficking (1-4). The utility of an S1P receptor agonist was unexpected indeed, prior speculation focused on the potential (as yet unrealized) for S1P antagonists as anti-angiogenic agents.

Recent findings also suggest a physiological influence for S1P in the vasculature. While not yet explored in detail, it has been hypothesized that S1P may mediate anti-inflammatory actions on endothelial cells through its release from high-density lipoprotein (HDL) (5). Furthermore, an $S1P_1$ receptor antagonist described herein blocked the anti-inflammatory action of S1P, thereby providing evidence that this effect maps to the $S1P_1$ receptor. If verified, this result would expand the role of the $S1P_1$ receptor to include influencing monocyte extravasation and further highlight how the development of S1P-receptor specific compounds is expanding our understanding of the biology of this important signaling system.

To characterize the biology associated with individual S1P receptors further, we have undertaken a program to develop S1P analogs with the twin goals of expanding the structure-activity relationships (SAR) associated with S1P receptor interactions and identifying receptor specific compounds. Our studies have lead to the identification of a series of S1P analogs that behave as antagonists at two of the five S1P receptors.

There is a long felt need in the art for S1P analogs which can modulate activity of more than one of the S1P receptors. The present invention satisfies these needs.

SUMMARY OF THE INVENTION

The present invention provides compounds that have antagonist activity at the $S1P_1$ and/or $S1P_3$ receptors, and/or are hydrolysis (phosphatases) resistant in biologic systems and/or have enhanced selectivity and potency at the $S1P_1$ and/or $S1P_3$ receptors. Accordingly there is provided an ester or a salt thereof, covalently bonded to one or two compounds of formula (I):

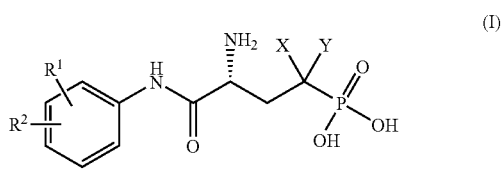

wherein X and Y are independently selected from the group consisting of hydrogen, OH, F, Cl, $PO_3$ or methyl or X and Y taken together with the atom to which they are attached form a keto group;

$R^1$ is selected from the group consisting of hydrogen, halo, tri-fluoromethyl, ($C_1$-$C_6$)-alkyl, ($C_1$-$C_6$) alkyl substituted with halo, hydroxy-, alkoxy, or cyano; and $R^2$ is selected from the group consisting of ($C_1$-$C_6$)alkyl, cycloalkyl substituted alkyl, ($C_2$-$C_6$)alkenyl, ($C_2$-$C_6$)alkynyl, aryl, alkyl substituted aryl, arylalkyl and aryl substituted arylalkyl; or a pharmaceutically acceptable ester thereof.

The present invention also provides esters of any of the compounds of the invention wherein the ester function can be added to form pro-drugs to increase oral availability.

The invention also provides compounds of formula (I) for use in medical therapy.

In another aspect, the present invention also provides:

a pharmaceutical composition comprising a compound of formula (I), or mixtures thereof or pharmaceutically acceptable salts, or esters thereof, and a pharmaceutically acceptable excipient (the composition preferably comprises an effective antagonist amount of the compound or salt);

a method of treating neoplastic diseases, comprising administering to a mammal (e.g., a human) in need of such treatment, a compound of formula (I) or pharmaceutically acceptable salts thereof;

a method for blocking angiogenesis (the formation blood vessels) in a tumor using a compound of the invention for treatment of neoplastic diseases;

a method for modulation of the immune system by altering lymphocyte trafficking for treatment of autoimmune diseases or prolongation of allograft transplant survival;

a method for treatment of cardiac arrhythmias;

a method for inhibiting angiogenesis in a tumor, comprising contacting (in vitro or in vivo) the cancerous cells with an effective inhibitory amount of a compound of formula I, or a pharmaceutically acceptable salt thereof.

a compound of formula (I) or a pharmaceutically acceptable salt thereof for use in medical treatment (e.g., the treatment of neoplastic disease, prolonging allograft transplant survival, for prevention of angiogenesis, alter lymphocyte trafficking, modulate the immune system, treatment of autoimmune diseases, or the treatment of cardiac arrhythmias);

the use of a compound of formula I or a pharmaceutically acceptable salt thereof to prepare a medicament for inhibiting angiogenesis in a tumor in a mammal (e.g., a human).

The invention also includes a method for binding a compound of formula I (e.g., $S1P_1/S1P_3$ receptor antagonists) to designated S1P receptor sites comprising said receptors, in vivo or in vitro, with an amount of a compound of formula I effective to bind to said receptors. Tissue comprising ligand bound designated S1P receptor sites can be used to measure the selectivity of test compounds for specific receptor subtypes, or can be used as a tool to identify potential therapeutic agents for the treatment of diseases or conditions associated with acetyl choline disfunction, by contacting said agents with said ligand-receptor complexes, and measuring the extent of displacement of the ligand and/or binding of the agent.

The invention also provides novel intermediates and processes disclosed herein that are useful for preparing compounds of formula (I), including the generic and specific intermediates as well as the synthetic processes described in the Charts and Examples herein.

Figure 1:
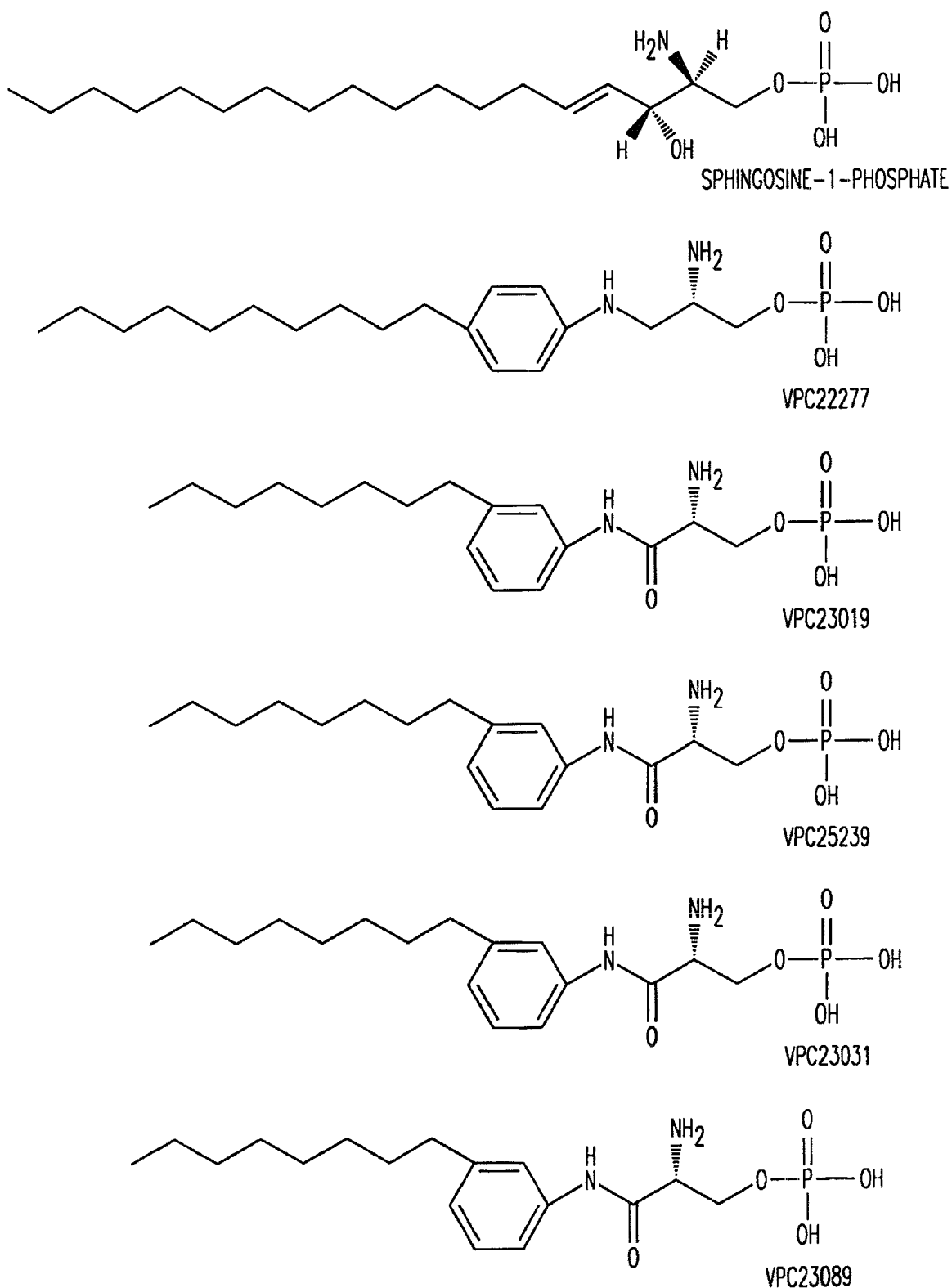
FIG. 1 illustrates the structures of Sphingosine-1-phosphate, and the compounds VPC22277, VPC23019, VPC23031, VPC23089 and VPC25239.

Panel D: illustrates the migration of T24 cells transfected stably with human $S1P_1$ receptor was observed with the $S1P_1$ agonist VPC22277 (10 nM) but not VPC23019 (1 nM-1000 nM). Data points are in duplicate and are representative of two independent experiments. The percent migration is based on normalization of relative fluorescence units (RFU) values obtained from the RFU values obtained the migration observed with 0.1% BSA carrier (minimum) and VPC22277 (maximum). Typical values for zero and 100% migration were approximately 30000 and 100000 RFU/well, respectively.

Panels E and F: illustrate the concentration dependent calcium mobilization of untransfected T24 cells (inset) and T24 cells transfected stably with human $S1P_3$ receptor was observed with S1P (filled circles) but not VPC23019 (open circles). Data points are in triplicate and are representative of two independent experiments. The percent activation is based on normalization of relative fluorescence units (RFU) values obtained from the minimum and maximum S1P concentration. Typical values for zero and 100% calcium mobilization were approximately 400 and 4000 RFU/well, respectively.

FIG. 3 (Panels A-D) Panels A and B illustrate the antagonism at the $S1P_1$ and $S1P_3$ receptors by VPC23019. HEK293T cells were transfected transiently with equal amounts of human $S1P_1$ or $S1P_3$ receptor and $G_{i2}\alpha$, $G\beta_1$, and $G\gamma_2$ plasmid DNAs. Membranes were collected after 60 hours. Receptor activation was determined using a broken-cell binding assay measuring the binding of $[\gamma^{35}S]GTP$ to the membrane as a function of agonist (S1P) stimulation. Blockade of S1P stimulation at $S1P_1$ and $S1P_3$ in the $[\gamma^{35}S]GTP$ broken-cell binding assay was performed in the absence (filled circles) or presence of 10000 nM (open circles), 1000 nM (open squares), and 100 nM (filled squares) concentrations of VPC23019. The binding constant ($pK_b$) is reported as $pK_b \pm S.E.M$. Data points are in hextuplicate and are representative of two independent experiments for each receptor. The percent activation is based on normalization of disintegrations per minute (dpm) values obtained from the minimum and maximum S1P concentration. Typical values for zero and 100% binding were approximately 300 and 3000 dpm/well, respectively, for both the human $S1P_1$ and $S1P_3$ receptors.

Panel C illustrates the blockade of the migration of T24 cells transfected stably with human $S1P_1$ receptor obtained with the $S1P_1$ agonist VPC22277 (10 nM) was observed with 10, 100 and 1000 nM concentrations of VPC23019. Data points are in duplicate and are representative of two independent experiments. The percent migration is based on normalization of relative fluorescence units (RFU) values obtained from the RFU values obtained the migration observed with BSA (minimum) and VPC22277 (maximum). Typical values for zero and 100% migration were approximately 30000 and 100000 RFU/well, respectively.

Panel D illustrates the $Ca^{2+}$ mobilization observed with T24 cells transfected stably with human $S1P_3$ receptor (solid line) was not altered by pre-treatment with VPC23019 (10000 nM-dashed line) followed by washout. Data points are in triplicate and are representative of two independent experiments. The percent activation is based on normalization of relative fluorescence units (RFU) values obtained from the minimum and maximum S1P concentration. Typical values for zero and 100% calcium mobilization were approximately 400 and 4000 RFU/well, respectively.

Figure 4A:
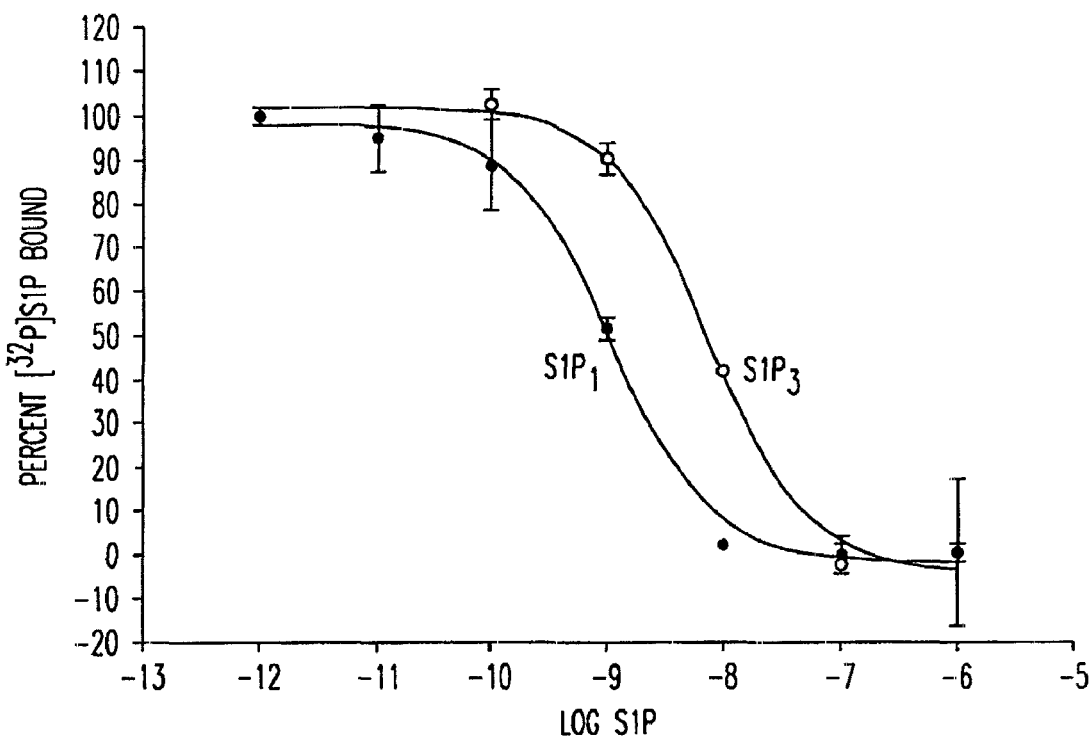

FIG. 4 (Panels A and B) illustrate the displacement of radiolabeled S1P by VPC23019 at $S1P_1$ and $S1P_3$. HEK293T cells were transfected transiently with equal amounts of human $S1P_1$ or $S1P_3$ receptor and $G_{i2}\alpha$, $G\beta_1$, and $G\gamma_2$ plasmid DNAs. Membranes were collected after 60 hours. Displacement of radiolabeled S1P was determined using a membrane binding assay measuring the binding of $[^{32}P]S1P$ to the receptor. Dose dependent displacement of $[^{32}P]S1P$ was observed with S1P (A) and VPC23019 (B) for both $S1P_1$ (closed circles) and $S1P_3$ (open circles) receptors. The $pK_i$ values are the −log of the inhibitory binding constant ($K_i$) and are reported as $pK_i \pm S.E.M$. Data points are in triplicate and are representative of two independent experiments for each receptor. The percent binding is based on normalization of disintegrations per minute (dpm) values obtained from the minimum and maximum. Typical values for zero and 100% binding were approximately 10000 and 30000 dpm/tube, respectively, for both the human $S1P_1$ and $S1P_3$ receptors. Non-specific binding was determined as residual binding of radioligand in the presence of excess S1P to membranes, both heat-denatured and non heat-denatured, from HEK293T cells transfected transiently with receptor and G-protein DNAs, and it was typically 60% of total binding.

Figure 5A:
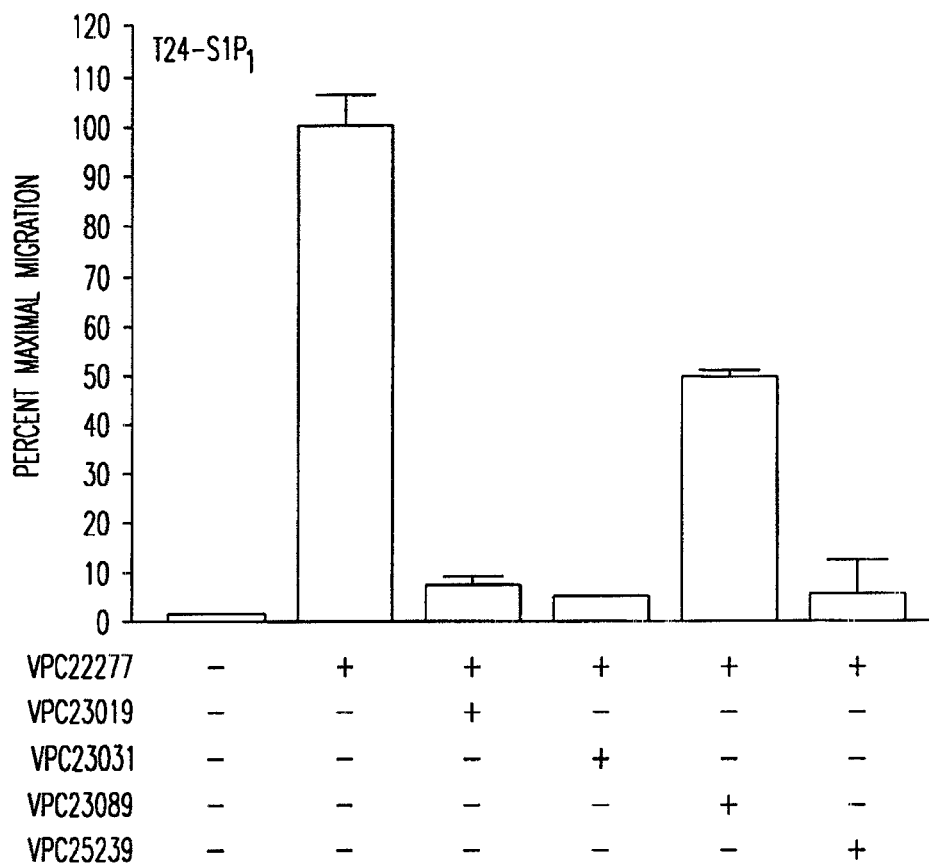
Figure 5B:
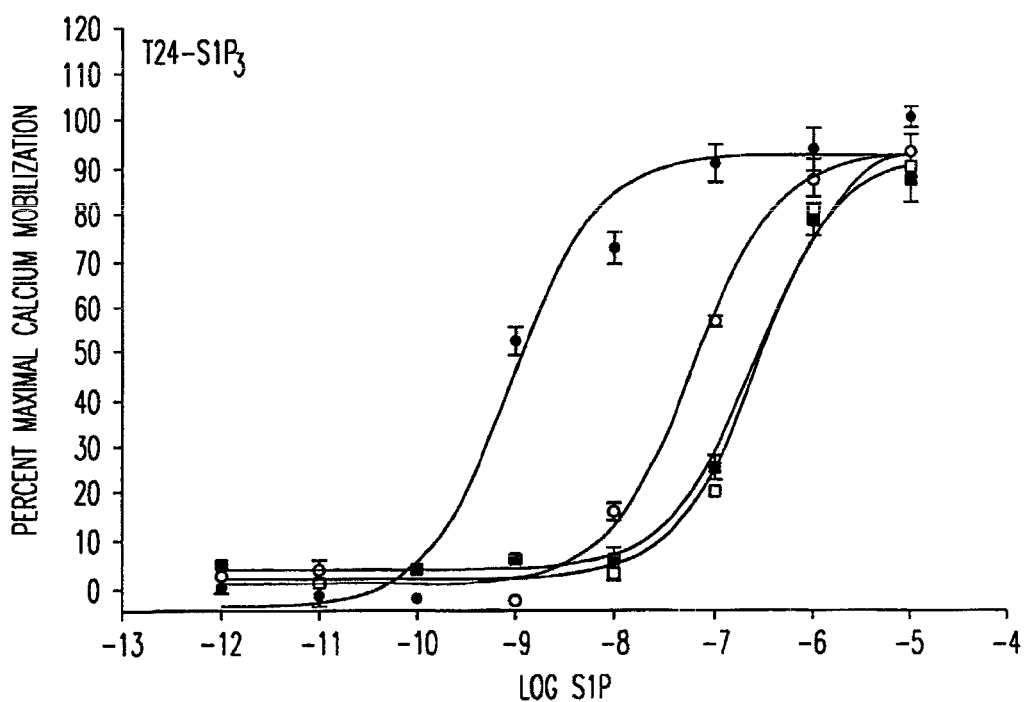

FIG. 5: (Panel A and B) illustrate the agonist response at the S1P$_1$ and S1P$_3$ receptors is altered by VPC23019-related analogs. Panel A: Blockade of the migration of T24 cells transfected stably with human S1P$_1$ receptor obtained with the S1P$_1$ agonist VPC22277 (10 nM) was observed with VPC23019, VPC23031, VPC23089, and VPC25239 (50 nM). Data points are in duplicate and are representative of two independent experiments. The percent migration is based on normalization of relative fluorescence units (RFU) values obtained from the RFU values obtained the migration observed with BSA (minimum) and VPC22277 (maximum). Typical values for zero and 100% migration were approximately 30000 and 100000 RFU/well, respectively.

Panel B: Blockade of Ca$^{2+}$ mobilization via stimulation of T24 cells transfected stably with human S1P$_3$ receptor was performed in the absence (filled circles) or presence of 10000 nM VPC23031 (filled squares), VPC23089 (open circles), and VPC25239 (open squares). Data points are in triplicate and are representative of two independent experiments. The percent activation is based on normalization of relative fluorescence units (RFU) values obtained from the minimum and maximum S1P concentration. Typical values for zero and 100% calcium mobilization were approximately 400 and 4000 RFU/well, respectively.

FIG. 6 (Panels A-B) illustrate synthetic schemes for the synthesis of compounds of the invention, particularly VPC44116.

Figure 7:
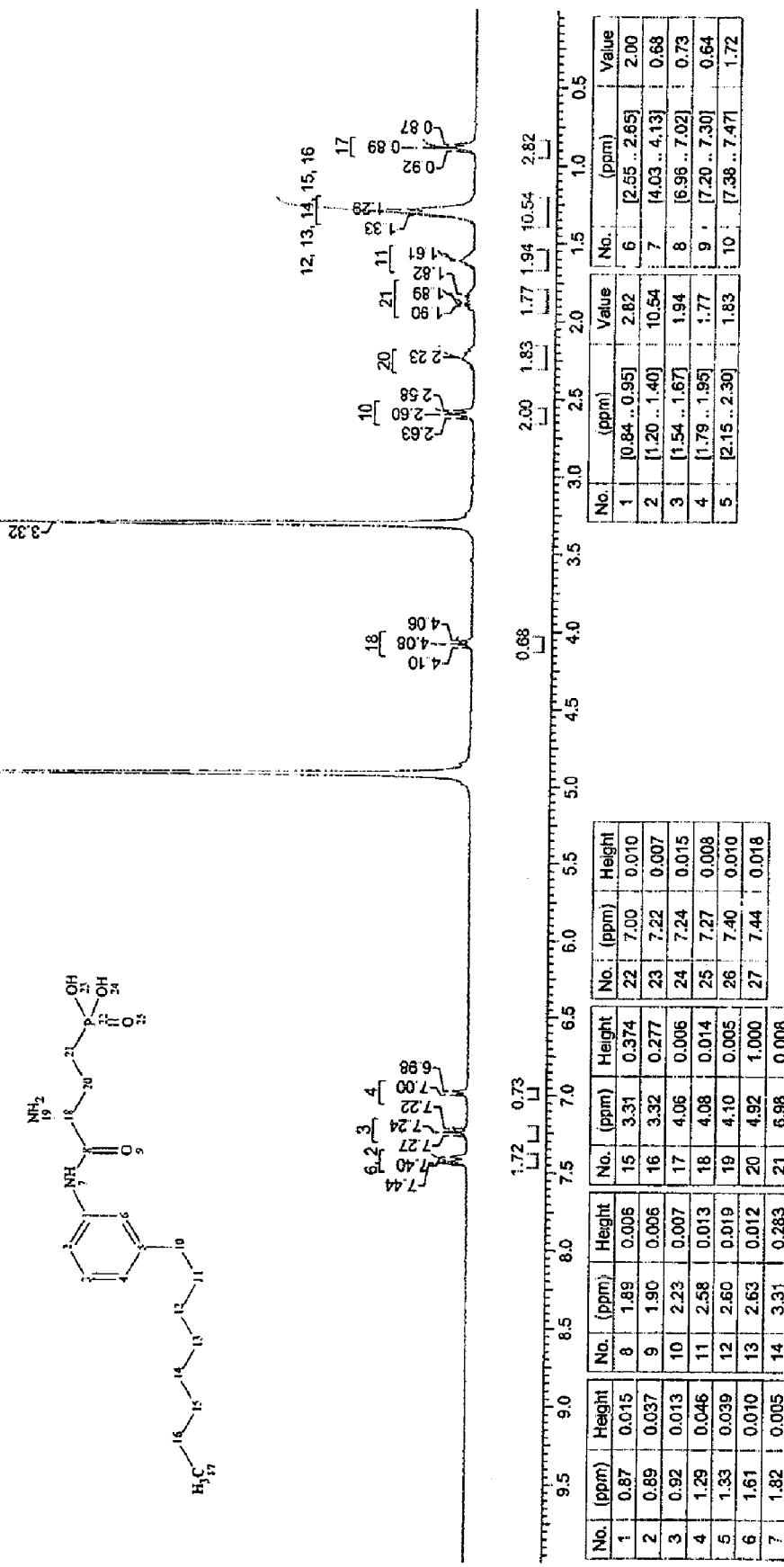

FIG. 7 is a $^1$H NMR spectrum of compound VPC44116, a compound of the invention.

Figure 8:
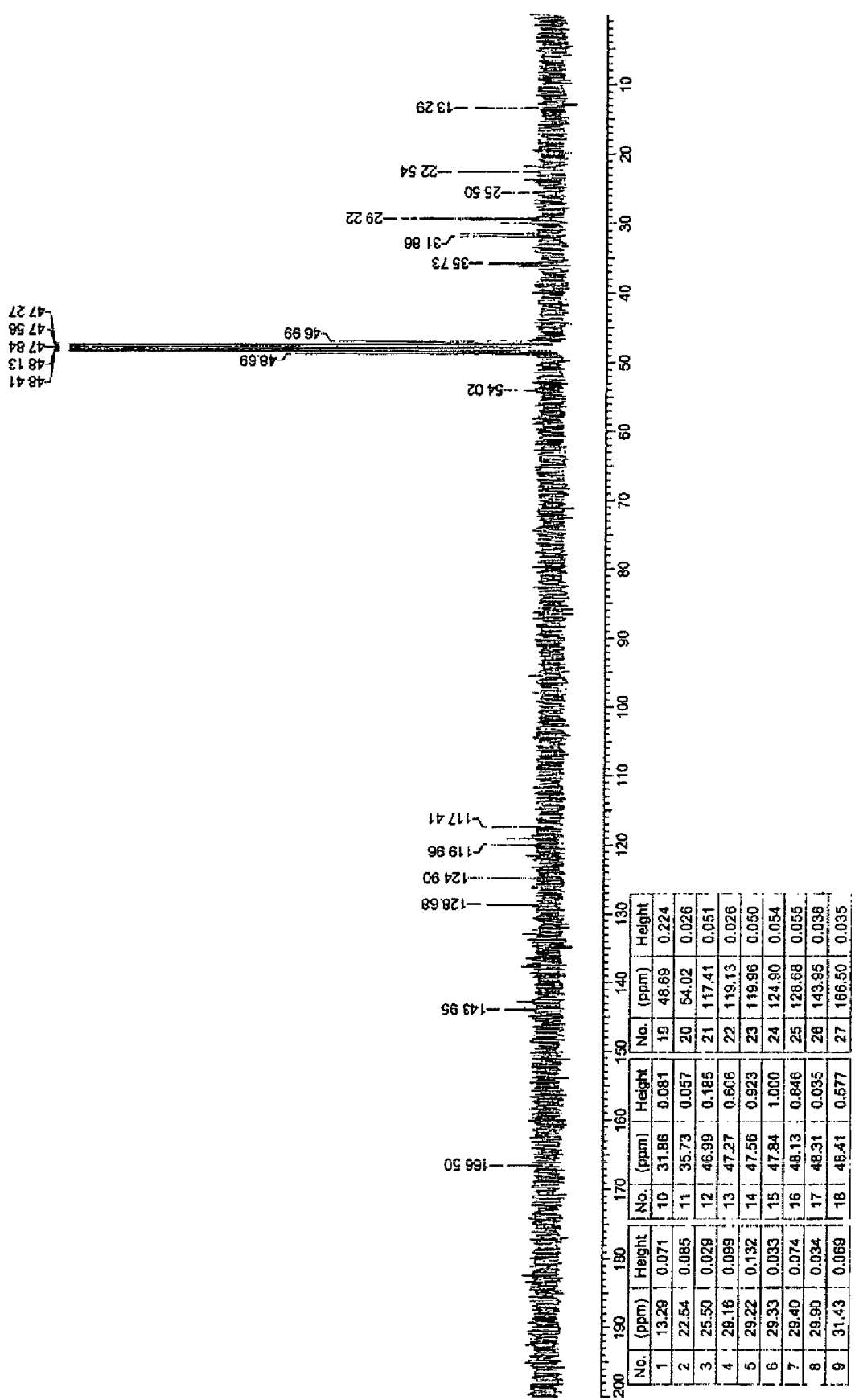

FIG. 8 is a $^{13}$C NMR spectrum of compound VPC44116, a compound of the invention.

DETAILED DESCRIPTION

Abbreviations

S1P, sphingosine-1-phosphate; GPCR, G-protein coupled receptor; SAR, structure-activity relationship; EDG, endothelial cell differentiation gene; EAE, experimental autoimmune encephalomyelitis; NOD non-obese diabetic; TNFα, tumor necrosis factor alpha; HDL, high density lipoprotein; RT-PCR, reverse transcriptase polymerase chain reaction

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred-values listed below for radicals, substituents, and ranges, are for illustration only, they do not exclude other defined values or other values within defined ranges for the radicals and substituents The articles "a" and "an" are used herein to refer to one or to more than one (i.e., to at least one) of the grammatical object of the article. By way of example, "an element" means one element or more than one element.

Receptor "antagonists" are defined as compounds that 1) lack intrinsic agonist activity and 2) block agonist (e.g., S1P) activation of the S1P receptor(s), often in a manner that is both fully surmountable and reversible ('competitive antagonist').

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "C$_1$-C$_6$ alkyl," as used herein, represents a branched or linear alkyl group having from one to six carbon atoms. Typically C$_1$-C$_6$ alkyl groups include, but are not limited to, methyl, ethyl, n-propyl, iso-propyl, butyl, iso-butyl, sec-butyl, tert-butyl, pentyl, hexyl and the like.

The term "C$_2$-C$_6$ alkenyl," as used herein, represents an olefinically unsaturated branched or linear group having from 2 to six carbon atoms and at least one double bond. Examples of such groups include, but are not limited to, 1-propenyl, 2-propenyl, 1,3-butadienyl, 1-butenyl, hexenyl, pentenyl, and the like.

The term "C$_2$-C$_6$ alkynyl," refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "C$_3$-C$_8$ cycloalkyl," represents cyclopropyl, cyclobutyl, cyclopentyl, cyclohexyl, cycloheptyl, cyclooctyl and the like.

As used herein, the term "optionally substituted" refers to from zero to four substituents, wherein the substituents are each independently selected. Each of the independently selected substituents may be the same or different than other substituents.

As used herein the term "aryl" refers to a mono or bicyclic carbocyclic ring system having one or two aromatic rings including, but not limited to, phenyl, benzyl, naphthyl, tetrahydronaphthyl, indanyl, indenyl, and the like.

As used herein "optionally substituted aryl" includes aryl compounds having from zero to four substituents, and a substituted aryl includes aryl compounds having one to three substituents, wherein the substituents include groups such as, for example, alkyl, halo or amino substituents.

The term (C$_5$-C$_8$ alkyl)aryl refers to any aryl group which is attached to the parent moiety via the alkyl group, and the term (C$_5$-C$_8$ alkyl)(C$_5$-C$_6$ aryl) refers to a five or six membered aromatic ring that is attached to the parent moiety via the C$_5$-C$_8$ alkyl group.

As used herein, the term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes prophylaxis of the specific disorder or condition, or alleviation of the symptoms associated with a specific disorder or condition and/or preventing or eliminating said symptoms.

As used herein, an "effective amount" means an amount sufficient to produce a selected effect. For example, an effective amount of an S1P receptor antagonist is an amount that decreases the cell signaling activity of the S1P receptor.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The method of the invention includes a kit comprising an inhibitor identified in the invention and an instructional material which describes administering the inhibitor or a composition comprising the inhibitor to a cell or an animal. This should be construed to include other embodiments of kits that are known to those skilled in the art, such as a kit comprising a (preferably sterile) solvent suitable for dissolving or suspending the composition of the invention prior to administering the compound to a cell or an animal. Preferably the animal is a human.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine S1P antagonist activity using the standard tests described herein, or using other similar tests which are well known in the art.

Processes for preparing compounds of formula I or for preparing intermediates useful for preparing compounds of formula I are provided as further embodiments of the invention. Intermediates useful for preparing compounds of formula I are also provided as further embodiments of the invention.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The present invention is directed to sphingosine 1-phosphate (S1P) analogs that have activity as receptor antagonists at one or more S1P receptors, specifically the S1P$_1$ and S1P$_3$ receptor types. The invention includes both compounds that have a phosphate moiety as well as compounds with hydrolysis-resistant phosphate surrogates such as phosphonates, alpha-substituted phosphonates particularly where the alpha substitution is a halogen and phosphothionates.

The disclosure provides herein that a subset of our aryl amide-containing compounds are antagonists at the S1P$_1$ and S1P$_3$ receptors. The lead compound in the series, VPC23019, was found in broken cell and whole cell assays to behave as a competitive antagonist at the S1P$_1$ and S1P$_3$ receptors. The SAR of this series is steep; for example, a slight modification of the lead compound resulted in VPC25239, which was one log order more potent at the S1P$_3$ receptor. These new chemical entities will enable further understanding of S1P signaling and provide leads for further S1P receptor antagonist development.

One embodiment of a S1P receptor antagonist is provided by the competitive antagonist compound VPC23019, which has the structure:

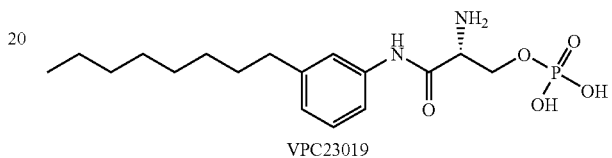

VPC23019

Sphingosine 1-phosphate (analogs as receptor antagonists}, antagonist activity is realized only when 1) the amino group is in the configuration shown (R in this case), 2) the alkyl chain is 8 carbon atoms (as shown) or less and 3) the alkyl chain is meta (as shown) or ortho, but not para, to the amide. Also, VPC23019 behaves as a competitive receptor antagonist at the human S1P$_1$ (pK$_b$=7.49±0.16) and human S1P$_3$ (pK$_b$=5.98±0.08) receptors but is an agonist at the human S1P$_4$ receptor (pEC$_{50}$=6.58±0.08) and a partial agonist at the human S1P$_5$ receptor (pEC$_{50}$= 7.07±0.12). VPC23019 is inactive as either an agonist or antagonist at the human S1P$_2$ receptor at concentrations up to 10 micromolar. Similar data for related antagonist compounds (VPC25239, alkyl chain 7 carbon atoms, meta; VPC23031, alkyl chain 6 carbons, meta; VPC23089, alkyl chain 8 carbons, ortho) is also found below. The salient difference among compounds in this series is that reduction of the alkyl chain from 8 (VPC23019) to 7 (VPC25239) carbon atoms results in a log order increase in potency at the S1P$_3$ receptor while leaving activities at other S1P receptor types relatively unchanged. As described further below, increasing the alkyl chain length to 9 or 10 carbon atoms (VPC23079, VPC23069, respectively), placing the alkyl chain in the para position (VPC22277), or placing the amino group in the other spatial orientation (VPC25027 (S enantiomer of VPC23019)), resulted in converting the compounds from antagonists to agonists (or partial agonists) at the S1P$_1$ receptor. The synthetic routes to all of the aforementioned compounds are described in the appended Davis et al. manuscript.

Another embodiment of a S1P receptor antagonist is provided by VPC44116, which has the structure:

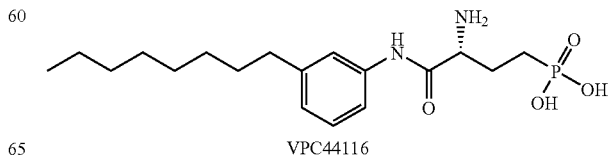

VPC44116

VPC44116 is the methylene phosphonate analog of VPC23019. VPC44116 is not described in the Davis et al. manuscript, which is restricted to phosphate-containing compounds. The antagonist properties of VPC44116 (potency, S1P receptor type selectivity) are indistinguishable from VPC23019. However, it is expected that VPC44116 will not be a substrate for the lipid phosphate phosphohydrolases that degrade lipids that contain phosphate monoesters (e.g. S1P, VPC23019). Thus VPC44116 is has been shown to have significantly increased metabolically stability in biologic systems, e.g., at least 18 hours, in a mouse.

Figure 6A:
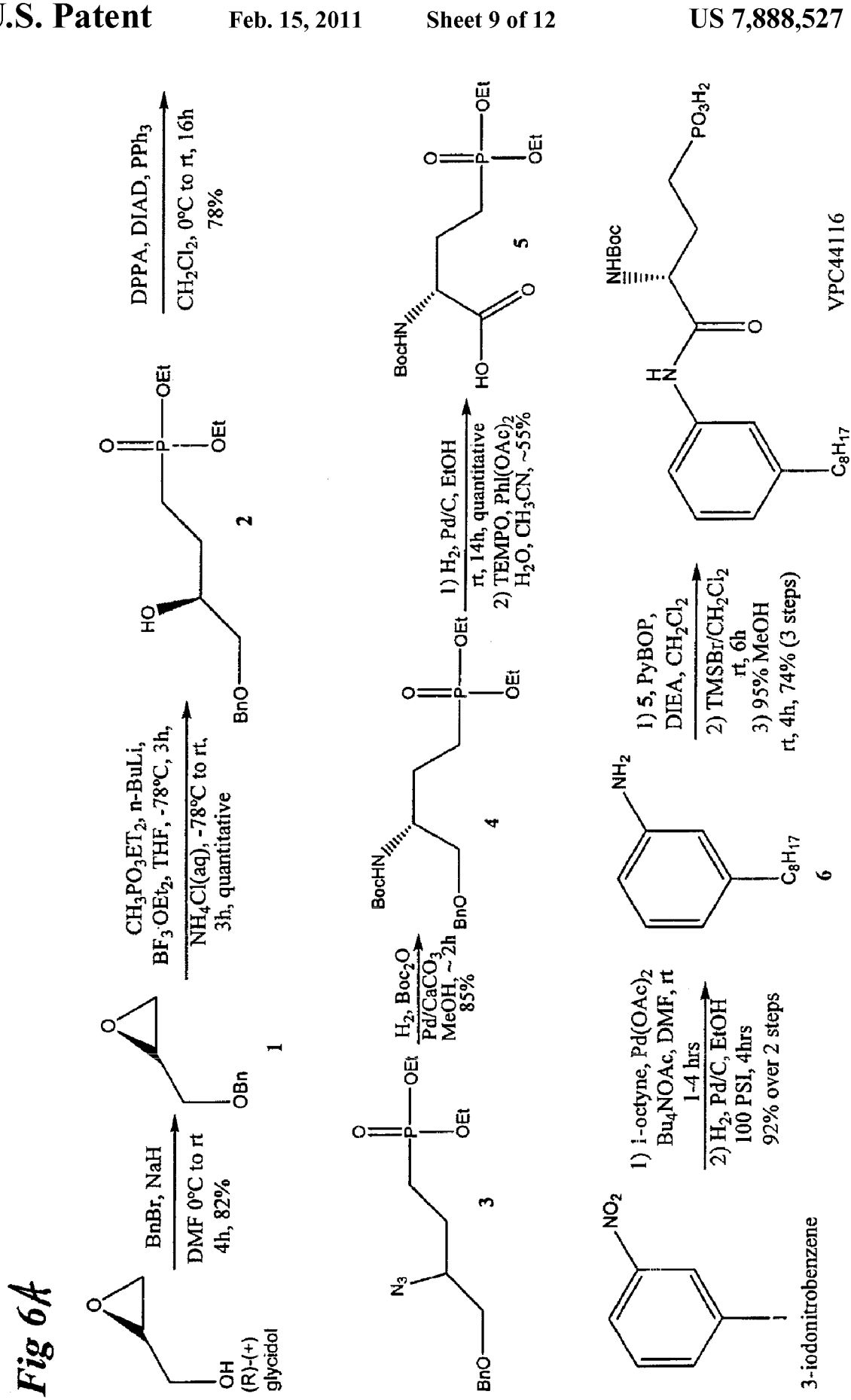
Figure 6B:
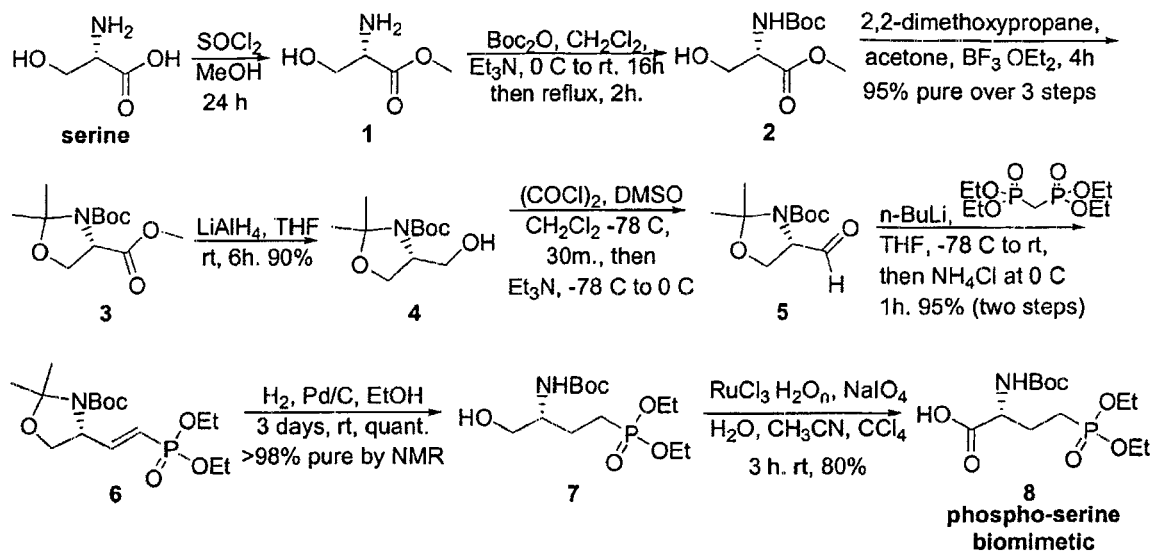
Figure 6B:
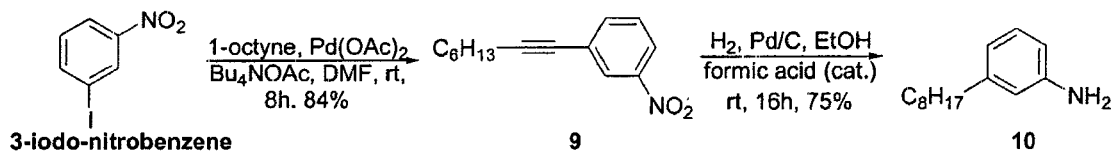
Figure 6B:
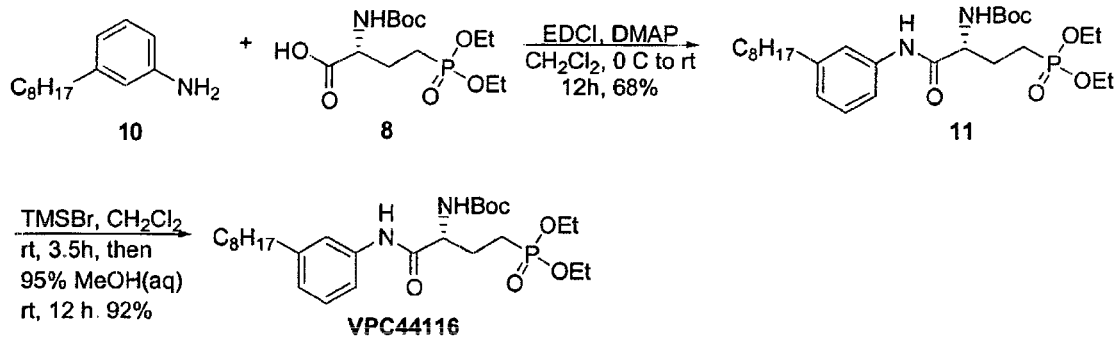

Synthetic routes to N-Boc protected specific compound of the invention, VPC44116 is illustrated in FIGS. 6A and 6B.

In a further embodiment of the invention, a compound (phosphothionate analog of VPC23019) with the formula (II) is expected to retain antagonist activity at the $S1P_1$ and $S1P_3$ receptors and to be hydrolysis (phosphatases) resistant in biologic systems:

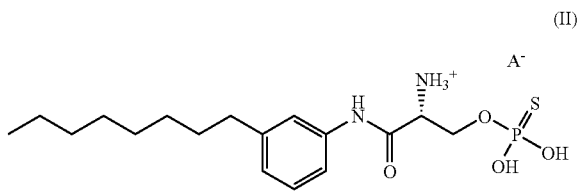

(II)

where $A^-$ represents a suitable counterion.

In a further embodiment of the invention, compounds with the formula (III) are expected to retain antagonist activity at the $S1P_1$ and $S1P_3$ receptors and to be hydrolysis (phosphatases) resistant in biologic systems:

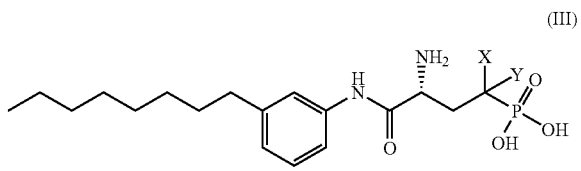

(III)

wherein X and Y are independently selected from the group consisting of hydrogen, OH, fluorine, chlorine, $PO_3$ or methyl; or X and Y together form a keto group; wherein the mono- or di-fluoro (F) compounds are preferred.

A specific value for lower alkyl group is ethyl or propyl

A specific value for X is fluorine or chlorine.

A specific value for X is fluorine.

A specific value for Y is fluorine or chlorine.

A specific value for Y is fluorine.

A specific value for X and Y and the atom to which they are attached form a >C=O group.

A specific compound of the invention has the $R^1$ group placed ortho or para to the amide.

A specific value for the alkyl groups in $R^2$ is chain lengths of 5-8 carbon atoms.

A specific compound of the invention has $R^2$ group placed ortho or meta to the amide.

A specific compound of the invention has $R^2$ group placed meta to the amide.

The invention also includes compounds having the formulas:

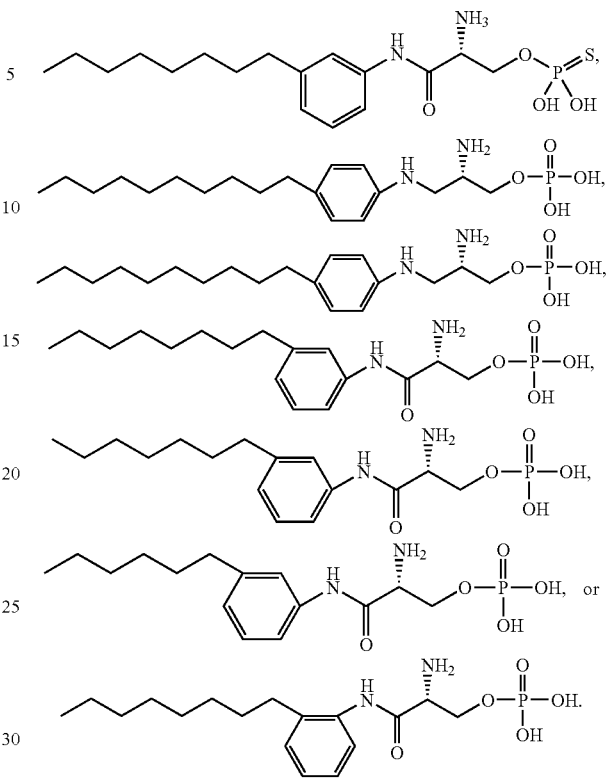

Processes for preparing compounds of formula (I) are provided as further embodiments of the invention and are illustrated by the following procedures in which the meanings of the generic radicals are as given above unless otherwise qualified.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, -ketoglutarate, and -glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Embodiments and Examples Materials and Methods:

Materials—Chemicals for syntheses were purchased from Aldrich Chemical Company (Milwaukee, Wis.), Sigma Chemicals (St. Louis, Mo.), Advanced ChemTech Chemical Company (Louisville, Ky.), and/or NovaBiochem Chemical Company (Laufelfingen, Switzerland) and were used without further purification. [γ-$^{32}$P]ATP and [γ-$^{35}$S]GTP were purchased from Amersham Pharmacia Biotech (Piscataway, N.J.). CyQuant Cell Proliferation Assay Kit and Fluo-4AM Calcium Indicator were purchased from Molecular Probes (Eugene, Oreg.). CHO and T24 cells were purchased from the American Type Culture Collection (Manassas, Va.). HEK293T cells were obtained from Dr. Judy White (Dept. of Cell Biology, University of Virginia, Charlottesville, Va.). Tissue culture media and normal FBS were obtained from Invitrogen (Carlsbad, Calif.). Charcoal/Dextran stripped FBS (CD-FBS) was obtained from Gemini Bio-Products (Woodland, Calif.). G-protein α, β and γ DNAs were a gift from Dr. Doug Bayliss (Dept. of Pharmacology, University of Virginia). Sphingosine 1-phosphate was purchased from Avanti Polar Lipids (Alabaster, Ala.).

Example 1

Syntheses of VPC23019, VPC23031, VPC25239 and VPC23089

The synthetic route to the meta-substituted compounds VPC23031, VPC25239 and VPC23019 is initiated with a Sonogashira coupling (6) of 3-iodo-1-nitrobenzene with the appropriate terminal alkyne. The resulting adducts are then subjected to simultaneous hydrogenation of the nitro group and the triple bond to generate the meta-substituted anilines. The anilines are next coupled to a protected serine and the ensuing amides underwent hydrogenolysis to afford the free alcohols. The alcohols are subsequently phosphorylated, oxidized with hydrogen peroxide and then subjected to acid catalyzed global deprotection to provide the final products, VPC23031, VPC25239 and VPC23019. Synthesis of the ortho-substituted compound, VPC23089, is commenced with the union of 2-iodoaniline and 1-octyne via a Sonogashira coupling. The ensuing aniline is then coupled to a protected serine utilizing the PyBOP reagent. The resulting amide is then subjected to a hydrogenation/hydrogenolysis step to remove the benzyl ether protecting group and simultaneously reduce the aryl triple bond. The liberated alcohol is next phosphorylated, oxidized with hydrogen peroxide and then subjected to acid catalyzed global deprotection to provide the final product VPC23089. NMR and mass spectrometry were used to confirm all structures. VPC23019 is available from Avanti Polar Lipids.

Example 1A

Synthesis of VPC44116

Compound VPC44116 was prepared as illustrated in FIGS. 6A and 6B. the N—BOC protecting group is removed using techniques known in the art. The $^1$H and $^{13}$C spectra from the product obtained are illustrated in FIGS. 7 and 8, respectively. Mass spectral data is as follows: MS m/z=371.9, 370.8 (base peak), 348.8, 270.5, 178.6.

Example 2

Transient Expression in HEK293T Cells

Figure 2A:
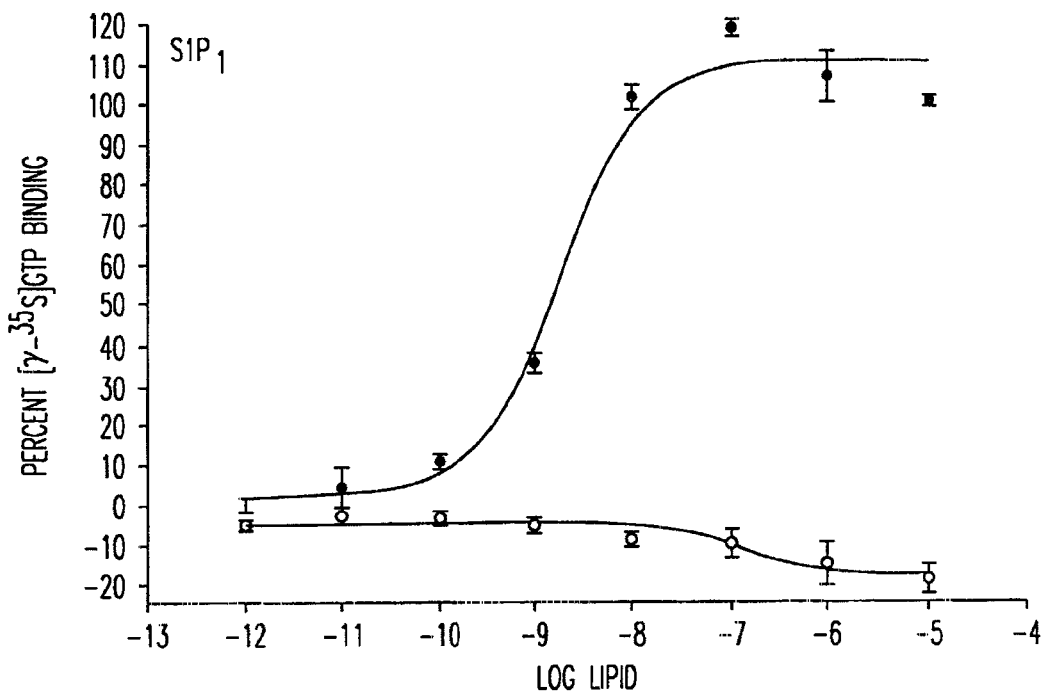
FIG. 2: (Panels A-F) illustrate the agonist activity at the $S1P_1$ and $S1P_3$ receptors. HEK293T cells were transfected transiently with equal amounts of human $S1P_1$ or $S1P_3$ receptor and $G_{i2}\alpha$, $G\beta_1$, and $G\gamma_2$ plasmid DNAs. Membranes were collected after 60 hours. Receptor activation was determined using a broken-cell binding assay measuring the binding of $[\gamma^{35}S]GTP$ to the membrane as a function of lipid concentration. Concentration dependent stimulation of $S1P_1$ (Panel A) and $S1P_3$ (Panel C) receptors was observed with S1P (filled circles) but not VPC23019 (open circles). When receptor plasmid DNA was excluded, no significant binding of $[\gamma^{35}S]GTP$ was observed with 10 μM S1P (Panel B), which demonstrates that the activity is a function of receptor expression. Binding of $[\gamma^{35}S]GTP$ was observed with 10 μM S1P in HEK393T cells transfected transiently with only receptor and $G_{i2}\alpha$ plasmid DNA; however the response was at least 3 fold less than that of cells where both receptor and all three G-protein plasmid DNAs were added (Panel B). Data points are in triplicate and are representative of two independent experiments. The percent activation is based on normalization of disintegrations per minute (dpm) values obtained from the minimum and maximum S1P concentration. Typical values for zero and 100% binding were approximately 300 and 3000 dpm/well, respectively, for both the human $S1P_1$ and $S1P_3$ receptors.
Figure 2B:
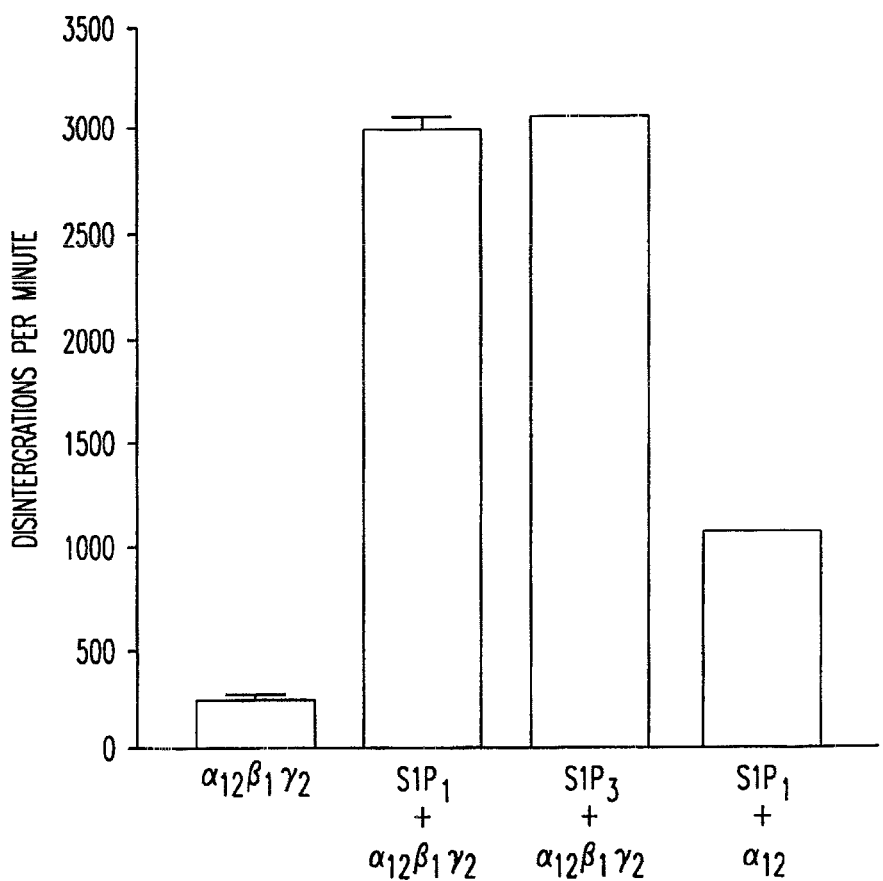

The appropriate receptor plasmid DNA (encoding human $S1P_1$, human $S1P_2$, human $S1P_3$, human $S1P_4$, human $S1P_5$, human $LPA_1$, human $LPA_2$ or human $LPA_3$ receptors) is mixed with equal amounts of expression plasmids encoding human $G_{i2}α$ (for $S1P_3$, a mutated (C352F) rat $G_{i2}α$ is used), cow $β_1$, and cow $γ_2$ proteins, and these DNAs are used to transfect monolayers of HEK293T cells (where 'T' indicates expression of the SV-40 virus large T antigen) using the calcium phosphate precipitate method (7). After about 60 hours, cells are harvested, membranes prepared, aliquoted, and stored at −70° C. until use (8). Transfection of receptor and G-protein is confirmed with the [γ-$^{35}$S]GTP binding assay (described below), as analysis of HEK293T cells transfected with G-proteins alone did not respond to agonist stimulation (See FIG. 2B).

Example 3

Stable Expression in T24 Cells 24 cell monolayers are co-transfected with the human $S1P_1$, $S1P_2$, $S1P_3$ receptor encoding DNAs and the pIRE-Spuro2 plasmid DNA (Clontech, San Jose, Calif.,) using either Lipofectamine 2000 (Invitrogen, Carlsbad, Calif.) or FuGENE 6 (Roche Applied Science, Indianapolis, Ind.). Clonal populations expressing the puromycin acetyltransferase gene are selected by addition of puromycin (Sigma-Aldrich, St. Louis, Mo.) to the culture media. T24 cells are grown in monolayers at 37° C. in a 5% $CO_2$/95% air atmosphere in growth media consisting of: 95% DMEM/F-12 medium and 10% charcoal/dextran stripped FBS.

Example 4

[γ-$^{35}$S]GTP Binding Assay

The [γ-$^{35}$S]GTP binding assay is performed as described previously (8). Membranes containing 1-5 μg of protein are incubated in 0.1 ml of binding buffer (in mM: HEPES/50, NaCl/100, $MgCl_2$/10, pH 7.5) containing 5 μg of saponin, 10 μM GDP, 0.1 nM [γ-$^{35}$S]GTP (1200 Ci/mmol), and indicated lipid(s) for 30 min at 30° C. and collected using a Brandel Cell Harvester (Gaithersburg, Md.). Samples are then analyzed for bound radionuclide.

Example 5

Cell Migration Assay

Cell migration assays are performed using modified Boyden chambers (tissue culture-treated, 24-mm diameter, 10-μm thickness, 8-μm pores, Transwell®; Costar Corp., Cambridge, Mass.) containing polycarbonate membranes that are coated on the underside with 0.1% gelatin. The underside of the polycarbonate membranes is rinsed once with migration media (DMEM/F12 without Phenol Red and 0.1% fatty acid free BSA) and then immersed in the lower chamber containing two milliliters of migration media. T24 cells transfected stably with human $S1P_1$ receptor DNA were grown in DMEM/F12 media containing charcoal/dextran stripped FBS and 10 µg/ml puromycin to 100% confluence in 150×2.5 mm tissue culture plates and serum starved at least 12 hours. Serum-starved cells were removed from culture dishes with 10× Trypsin-EDTA (Hanks' balanced salt solution containing 5 mM EDTA and 25 mM HEPES, pH 7.2, and 0.1% trypsin; Invitrogen, San Diego, Calif.), suspended in migration buffer and collected by centrifugation at 130×g for 5 minutes. The supernatant fluid was removed by aspiration and cell pellet resuspended in migration media ($10^6$ cells/ml). One milliliter of cell suspension was added to the top of each migration chamber and S1P agonist VPC22277 (10 nM) was added to the lower chamber. Cells were allowed to migrate to the underside of the membrane for 4 hours at 37° C. in the presence or absence of antagonist [VPC23019 (0 nM-1000 nM), VPC23019, VPC23031, VPC23089, and VPC25239 (all 50 nM)], which were added to the lower chamber. The non-migrating cells in the upper chamber were removed by aspiration and the migratory cells attached to the bottom surface of the membrane were isolated by incubation in 10× Trypsin-EDTA for 1 min at room temperature and gently tapping the plate to dislodge cells from the membrane. The mass of migratory cells per membrane was evaluated by combining 100 µl of cell suspension with an equal volume of CyQuant dye solution (3.0 ml of 2× lysis buffer and 15 µl CyQuant dye), and the resulting fluorescence quantified using the FlexStation™ fluorimeter (Molecular Devices, Menlo Park, Calif.). Each determination represents the average of two individual migration chambers. For determination of the reversibility of the antagonism associated with VPC23019, cells were incubated with 10 µM VPC23019 at 37° C. for 30 minutes. The monolayer was washed three times with phosphate buffered saline and processed immediately for the cell migration assay, as described above.

Example 6

Measurement of Intracellular Calcium Mobilization

A FlexStation™ fluorimeter (Molecular Devices, Menlo Park, Calif.) was used to measure intracellular calcium in native T24 cells and T24 cells transfected stably with either human $S1P_2$ or human $S1P_3$ receptor DNA. Cells were seeded (~50,000 cells/well) in 96-well, clear bottom black microplates (Corning Costar Corp.) and left overnight at 37° C. The cells were dye-loaded with 4 µM Fluo-4AM ester in a loading buffer (Hank's Balanced Salt Solution, pH 6.4, containing 20 mM HEPES, 0.1% fatty acid free BSA, and 2.5 mM probenecid) for 30 minutes at 37° C. After washing cell monolayers three times with phosphate buffered saline, loading buffer was added and the cells exposed to sets of compounds for 3 minutes at 25° C. in the FlexStation™. In all cases, each concentration of every compound was tested in at least triplicate. For determination of the reversibility of the antagonism associated with VPC23019 (10 µM), the compound was added in combination with loading dye to the cells and incubated at 37° C. for 30 minutes. The cells were washed with phosphate buffered saline and exposed to compounds immediately, as described above.

Example 7

Determination of the Binding Constant for VPC23019 at the $S1P_1$ and $S1P_3$ Receptors The binding constant ($K_b$) for VPC23019 at the $S1P_1$ and $S1P_3$ receptors was determined by Schild analyses from curves that were fitted using the nonlinear regression method discussed by Lew and Angus (9). Briefly, nonlinear analysis of the best-fit line generated by plotting the negative log of the $EC_{50}$ values obtained from agonist dose-response curves, in the absence and presence of varying concentrations of antagonist, was plotted against the concentration of antagonist to give the $K_b$ value. A F-test analysis was also performed to establish whether the antagonist did or did not meet the criteria of a simple competitive interaction.

Example 8

S1P Radio-Labeling

[$^{32}$P]-S1P was prepared by incubating sphingosine and [γ-$^{32}$P]ATP with cell lysate from HEK293T cells transiently transfected with human sphingosine kinase type 2 DNA. The 200 µl reaction contained 0.025 mM sphingosine, 1 mCi [γ-$^{32}$P]ATP (7000 Ci/mmol) and kinase buffer (in mM: $Mg(C_2H_3O_2)2$ (in 50 mM Tris, pH 7.5)/10, NaF/10, and semicarbizide/2). The reaction was initiated by the addition of 20 µg of cell lysate and incubated at 37° C. for at least 30 minutes. The [$^{32}$P]S1P was extracted by the addition of 1.0N HCl, 2.0M KCl, methanol and chloroform to the reaction mixture, vortexed, and centrifuged at 1000×g for 5-10 minutes. The organic layer was isolated and the extraction procedure repeated two additional times with the remaining aqueous fraction. The combined organic fractions were dried under a stream of nitrogen gas and resuspended in aqueous 0.1% fatty acid free BSA. The specific activity of the product, [$^{32}$P]S1P, is estimated to be that of the radio-labeled substrate, [γ-$^{32}$P]ATP, i.e., 7,000 Ci/mmol.

Example 9

[$^{32}$P]S1P Binding Assay

Membranes containing 5 µg of protein from HEK293T cells transfected transiently with both receptor and G-protein DNAs were incubated in 0.5 ml of binding buffer (in mM: HEPES/50, NaCl/100, $MgCl_2$/10, pH 7.5), 50 pM [$^{32}$P]S1P, and indicated lipid(s) for one hour at room temperature. Bound ligand was separated from free ligand by rapid filtration and analyzed in a liquid scintillation counter. Non-specific binding was determined as residual binding of radioligand in the presence of excess S1P to membranes, both heat-denatured and non heat-denatured, from HEK293T cells transfected transiently with receptor and G-protein DNAs, and it was typically 60% of total binding. The binding constant ($K_i$) associated with the ligand-receptor interaction was determined from the $IC_{50}$ using the Chang-Prusoff equation ($K_i=IC_{50}/(1+[L]/K_d)$. In applying this equation, the concentration of radioligand (L) is 0.05 nM and the $K_d$ value used was that reported for the S1P-$S1P_1$ receptor interaction, i.e. 8.1 nM (12).

Statistical Analysis. The $EC_{50}$ and $IC_{50}$ values for all dose response curves were determined by nonlinear regression analysis of all data using the Graphpad Prism© program. The error associated with the data collected is reported as the standard error of the mean (S.E.M).

Example 10

Results

VPC23019 is Devoid of Agonism at the $S1P_1$ and $S1P_3$ Receptors.

Figure 2C:
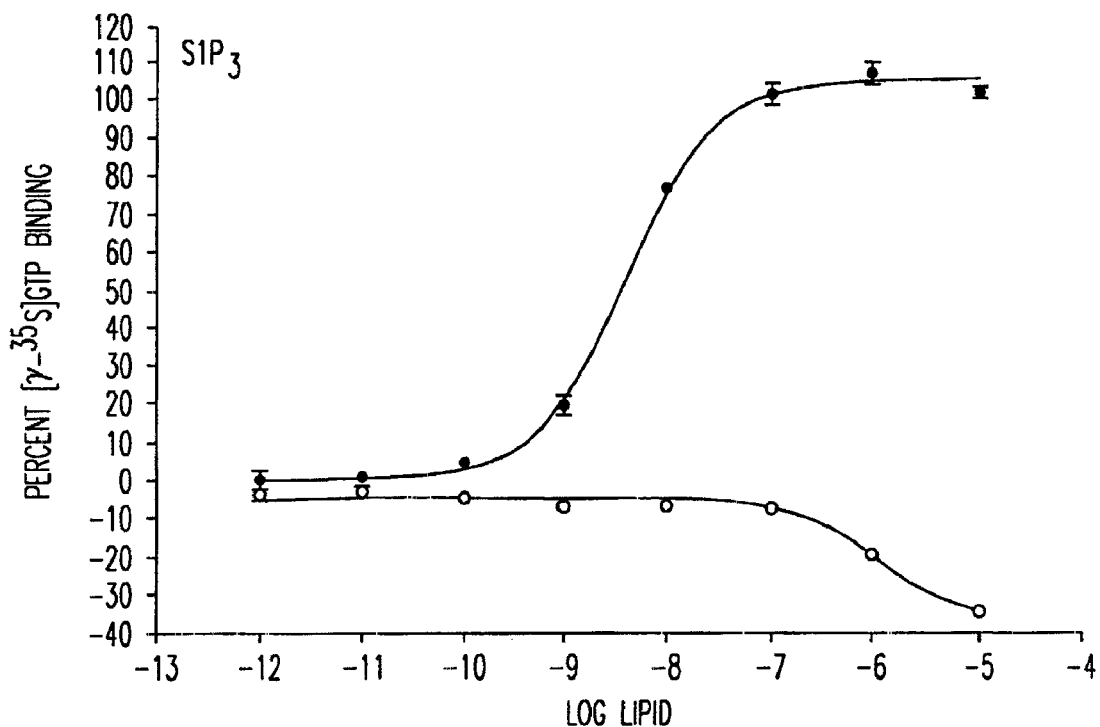

In the course of our examinations of S1P analog SAR, we discovered that the aryl-amide compound VPC23019 (FIG. 1) lacked agonist activity at the $S1P_1$ (FIG. 2A) and $S1P_3$ (FIG. 2C) receptors in a broken-cell [$\gamma$-$^{35}$S]GTP binding assay. Indeed, a profile suggesting inverse agonism was observed at VPC23019 concentrations greater than 100 nM in this assay; however, conformation of this activity in the presence of a neutral antagonist would required to define the observations with VPC23019 at these concentrations as inverse agonist activity. As such compounds are not available, it is possible that the decrease in [$\gamma$-$^{35}$S]GTP binding observed at these concentrations may be due to VPC23019 alteration of endogenous membrane-related agonist activity. This lack of agonist activity was confirmed in whole-cell assays using T24 cells (derived from bladder carcinoma) where either the $S1P_1$ (T24-$S1P_1$) or $S1P_3$ (T24-$S1P_3$) receptor were expressed stably. RT-PCR analysis detected only $S1P_2$ receptor mRNA endogenously in T24 cells; however, while the efficacy of the response was the same, S1P was at least 100-fold more potent when recombinant $S1P_1$, $S1P_2$, or $S1P_3$ (FIG. 2E) receptor were expressed stably. Thus, the T24 cells system provides an opportunity to interrogate individual S1P receptors introduced by transfection. Numerous studies have demonstrated that S1P can promote cell migration; however, it was shown recently that S1P can also inhibit migration, possibly through stimulation of the $S1P_2$ receptor (10). To circumvent this inhibitory effect, we used VPC22277 (FIG. 1), an S1P analog that is an agonist at the $S1P_1$ and $S1P_3$ receptors, but not the $S1P_2$ receptor (Table 1)—(all of the compounds in the aryl amide series (11) are devoid of any activity at the $S1P_2$ receptor). The $pEC_{50}$ values are the –log molar concentration of compound resulting in 50% of maximal [$\gamma$-$^{35}$S]GTP binding. The $pEC_{50}$ values are reported as $pEC_{50}$±S.E.M.

Figure 2D:
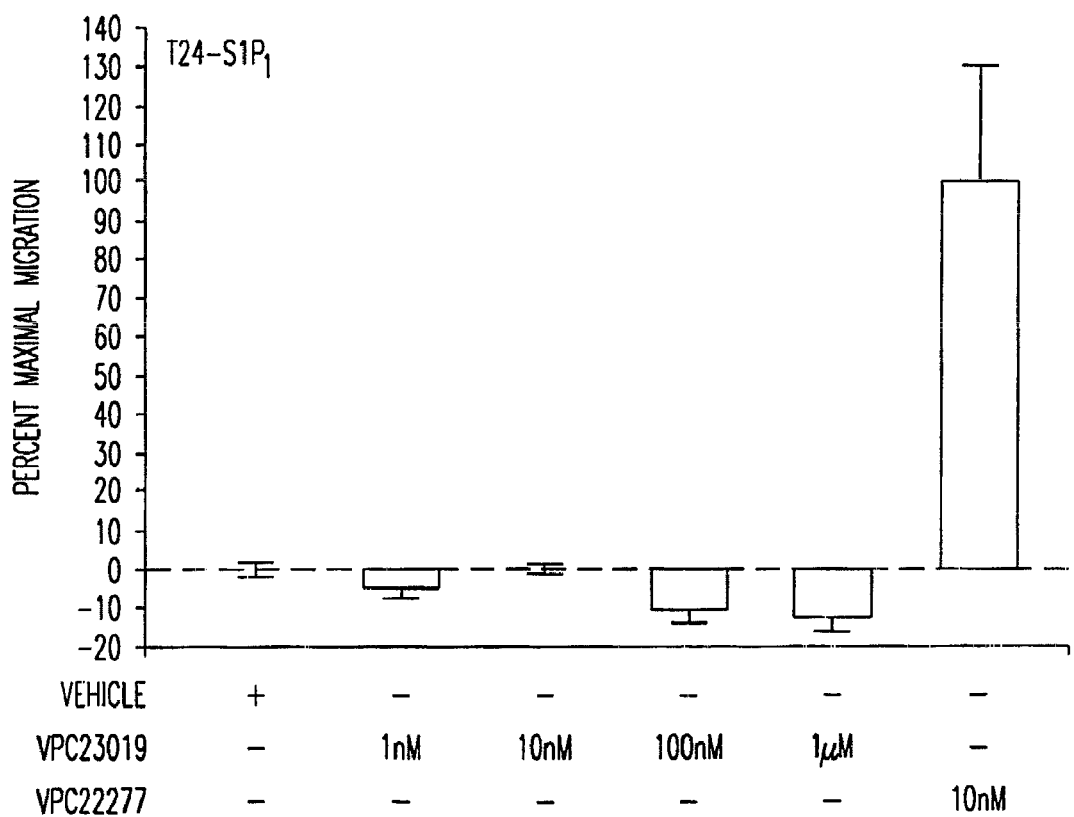
Figure 2E:
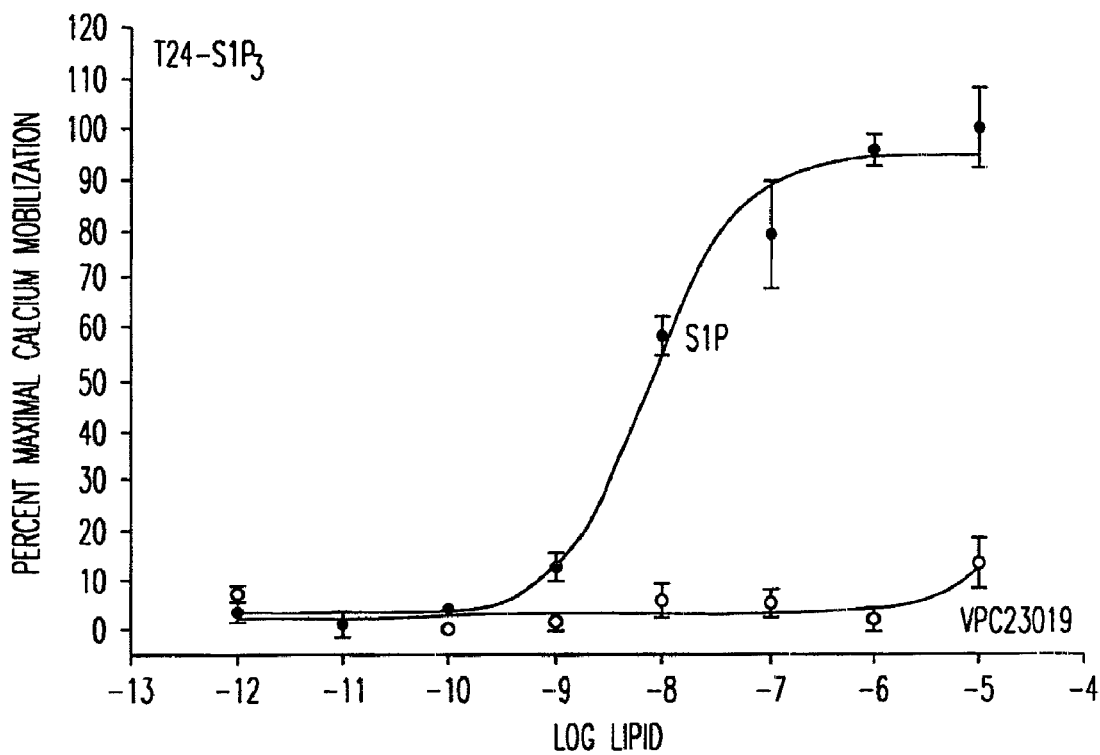
Figure 2F:
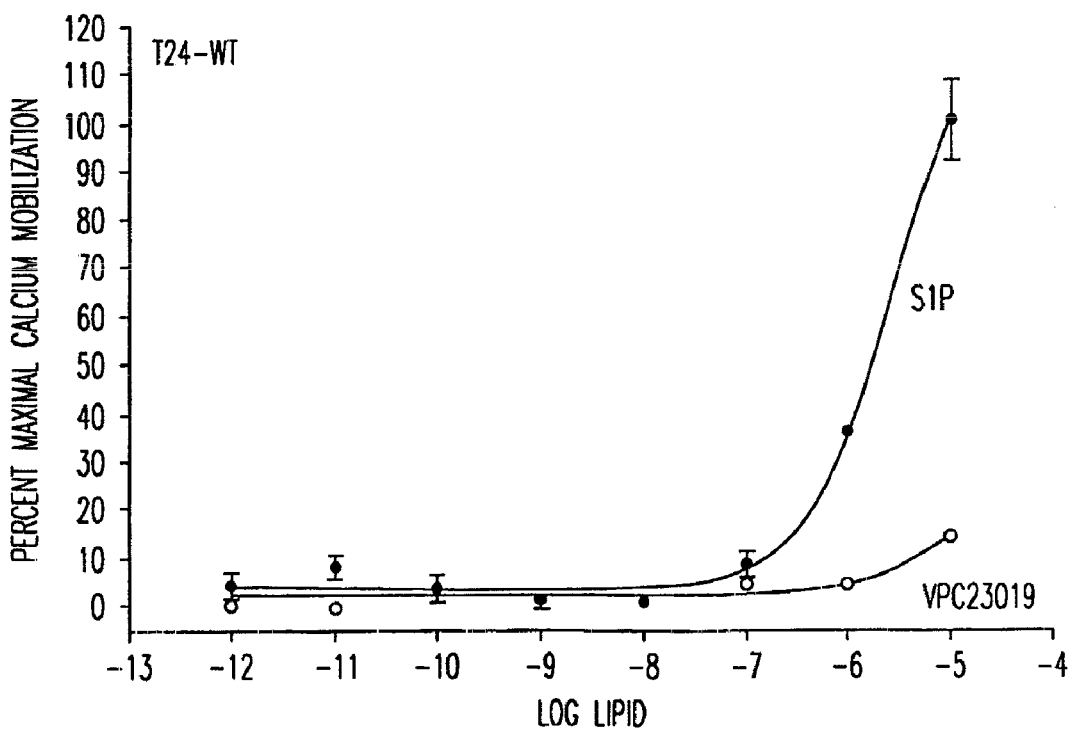
Figure 3A:
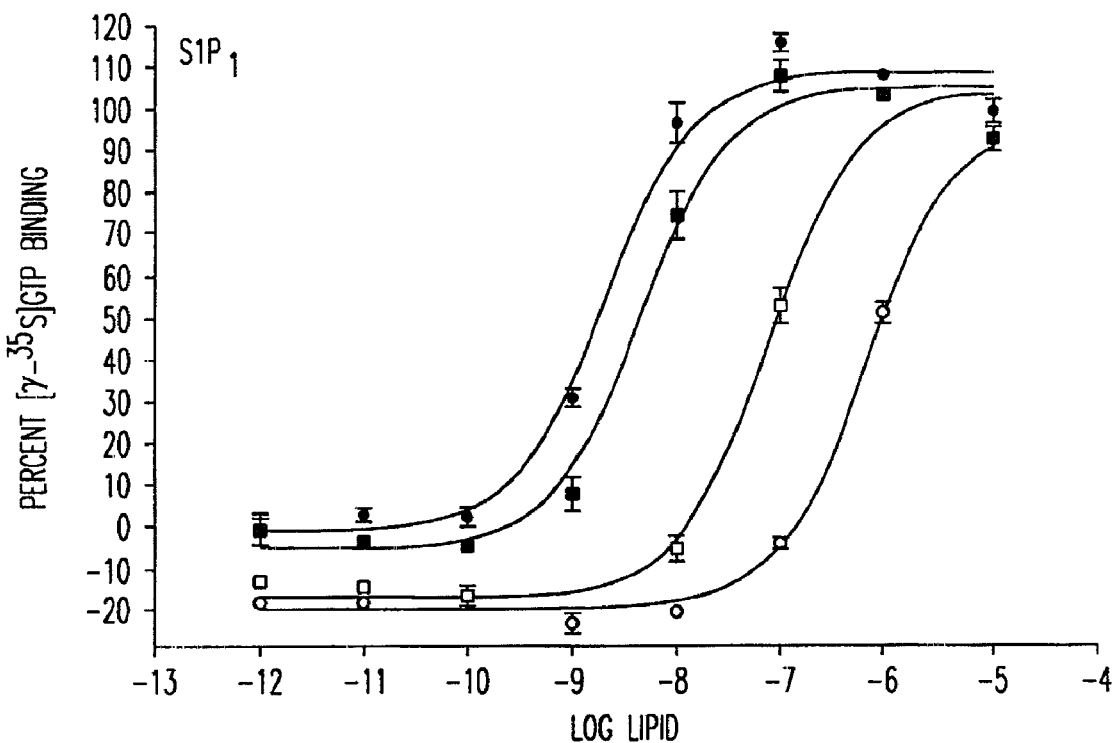
Figure 3B:
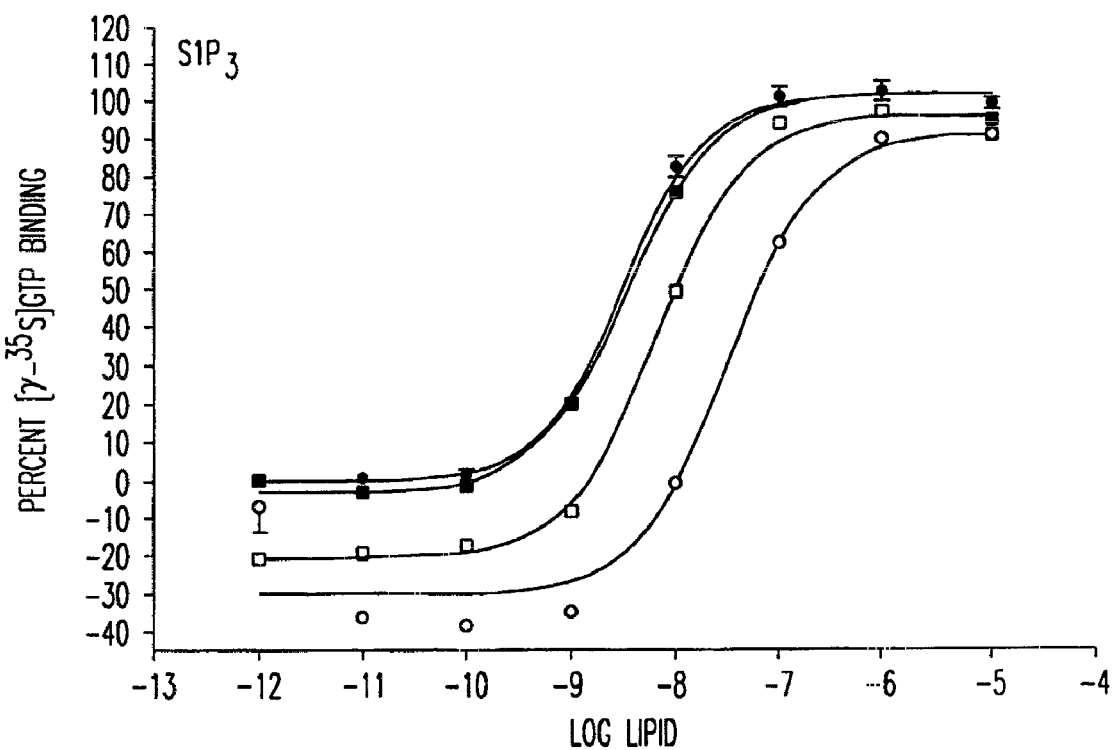
Figure 3C:
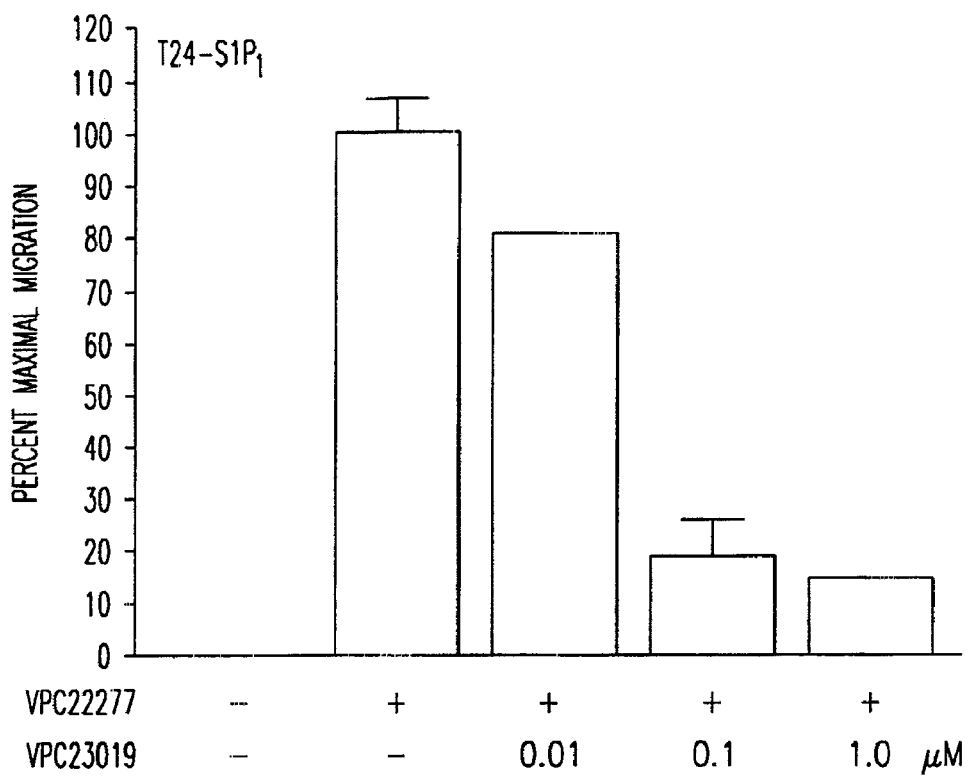
Figure 3D:
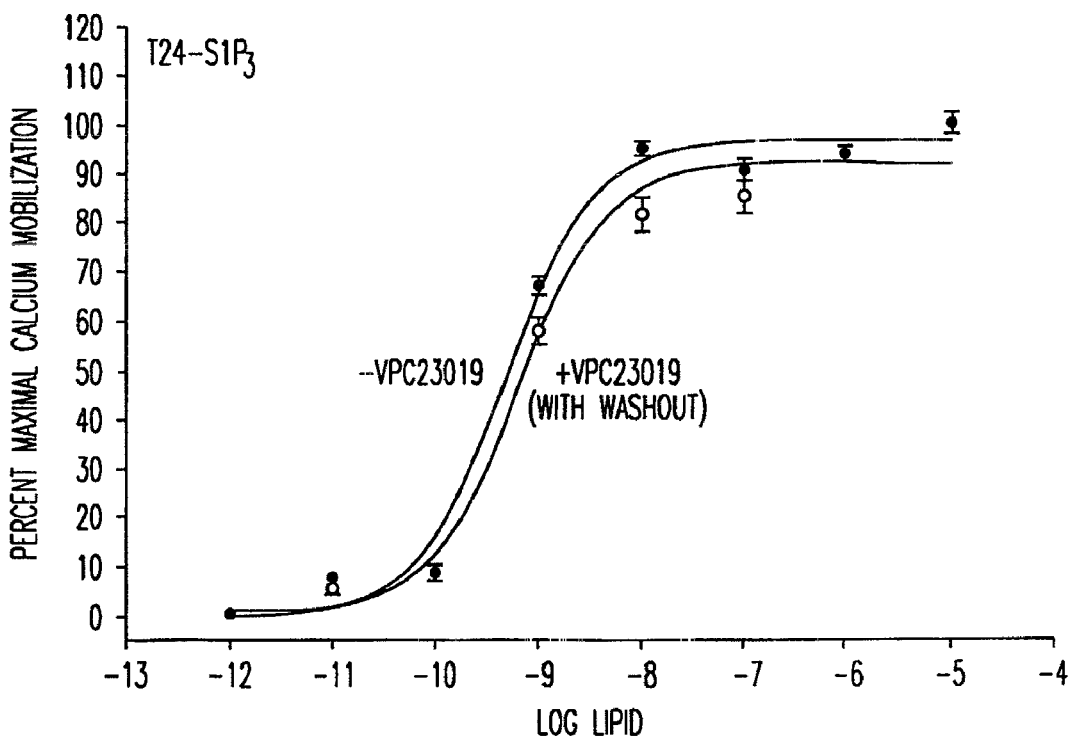

It was also found that migration of T24-$S1P_1$ cells could be induced by VPC22277, while no migration was evoked in response to VPC23019 (FIG. 2D). Similarly, in whole-cell calcium mobilization studies using T24-$S1P_3$ cells, dose-dependent calcium mobilization was observed with S1P and VPC23019 (FIG. 2E); however, this activity is not a result of stimulation of the $S1P_3$ receptor, as VPC2301-mediated calcium mobilization was observed with wild-type T24 cells (FIG. 2F). Thus, VPC23019 is devoid of agonist activity at the $S1P_1$ and $S1P_3$ receptors using both broken cell and whole cell assays.

VPC23019 Blocks Agonist Activity at the $S1P_1$ and $S1P_3$ Receptors.

The finding that VPC23019 exhibited inverse agonist activity at the $S1P_1$ or $S1P_3$ receptors prompted us to investigate whether this compound blocked agonist activity. Using the [$\gamma$-$^{35}$S]GTP binding assay, we found that incubation of S1P with increasing concentrations of VPC23019 at either the $S1P_1$ (FIG. 3A) or $S1P_3$ (FIG. 3B) receptors produced a dose-dependent, parallel rightward shift in the S1P concentration-effect curves. This shift in agonist-mediated responses was observed also in two whole cell assays—cell migration (FIG. 3C) and calcium mobilization. VPC23019 exhibited neither agonist activity at the $LPA_{1-3}$ EDG-family receptors at concentrations up to 30 μM, nor blocked LPA's action at these sites.

VPC23019 S1P Receptor Affinity.

Schild analyses of the antagonist action associated with VPC23019 in the [$\gamma$-$^{35}$S]GTP binding assay gave $pK_b$ values at the $S1P_1$ (FIG. 3A) and $S1P_3$ (FIG. 3B) receptors of 7.49±0.15 and 5.98±0.08, respectively. Additionally, the non-linear regression method of Lew and Angus (9), which predicts whether a compound behaves as a competitive antagonist, suggested VPC23019 behaves as a competitive antagonist at both receptors. Schild analysis of calcium mobilization in T24-$S1P_3$ cells gave a $K_b$ value for VPC23019 that was approximately 10-fold less than that observed in the

TABLE 1

Agonist activity at the S1P receptors

| Compound | Longest Alkyl Chain | Ring Subst. | Enantiomer | $pEC_{50}s$ | | | | |
|---|---|---|---|---|---|---|---|---|
| | | | | $S1P_1$ | $S1P_2$ | $S1P_3$ | $S1P_4$ | $S1P_5$ |
| S1P | 18 | — | S | 8.39 ± 0.02 | 8.62 ± 0.10 | 8.65 ± 0.11 | 6.81 ± 0.14 | 8.63 ± 0.06 |
| VPC22277 | 10 | para | R | 8.80 ± 0.06 | <5 | 7.13 ± 0.11 (pa) | 7.05 ± 0.22 (pa) | 7.96 ± 0.10 |
| VPC23019 | 8 | meta | R | na | <5 | na | 6.58 ± 0.08 | 7.07 ± 0.12 (pa) |
| VPC25239 | 7 | meta | R | na | <5 | na | 6.78 ± 0.09 | 7.94 ± 0.09 (pa) |
| VPC23031 | 6 | meta | R | na | <5 | na | 5.96 ± 0.06 | 6.87 ± 0.16 (wpa) |
| VPC23089 | 8 | ortho | R | na | <5 | na | 6.07 ± 0.21 | <5 |
| VPC23079 | 9 | meta | R | 6.17 ± 0.24 | <5 | na | 5.93 ± 0.08 | na |
| VPC23069 | 10 | meta | R | 7.09 ± 0.16 | <5 | 5.72 ± 0.28 (wpa) | 6.07 ± 0.07 | <5 |
| VPC25027 | 8 | meta | S | 8.65 ± 0.16 (pa) | <5 | na | 6.05 ± 0.04 | 7.20 ± 0.08 (pa) | na: no agonist activity (<10% of S1P $E_{max}$)
wpa: weak partial agonist activity (10-50% of S1P $E_{max}$)
pa: partial agonist activity (50-85% of S1P $E_{max}$)

[γ-$^{35}$S]GTP binding assay. However, the nonlinear regression analysis indicated that VPC23019 did not behave as a competitive antagonist in the calcium mobilization assay with T24-S1P$_3$ cells. Importantly, both whole-cell S1P receptor assays (Ca$^{2+}$ mobilization (S1P$_3$—FIG. 3D) and cell migration (S1P$_1$—not shown)) recovered fully after washing out the antagonist. Thus, the antagonism exhibited by VPC23019 is reversible as well as fully surmountable—essential criteria for a-competitive antagonist.

Figure 4B:
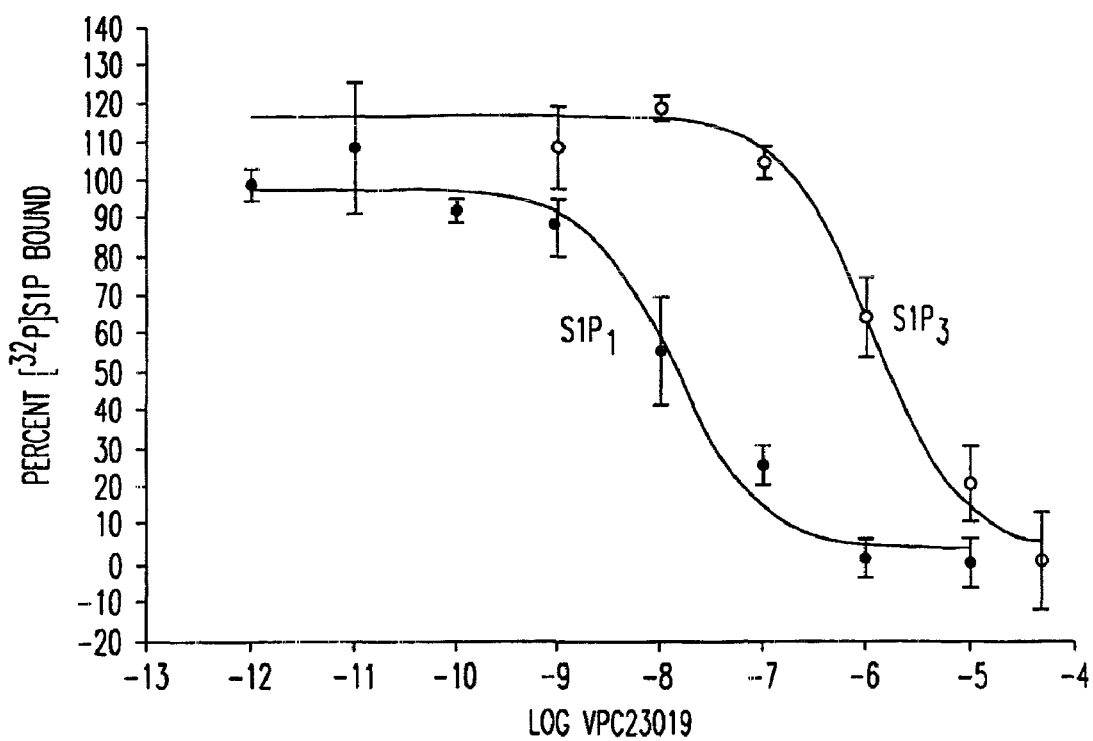

To measure the affinity of VPC23019 for the S1P$_1$ and S1P$_3$ receptors directly, we examined the ligand-receptor interaction associated with the S1P$_1$ and S1P$_3$ receptors via a receptor binding assay using [$^{32}$P]S1P in competition with S1P and VPC23019. Analysis of S1P in the radioligand binding assay (FIG. 4A) yielded pK$_i$ values of 8.96 and 8.12 at the S1P$_1$ and S1P$_3$ receptors, respectively. These values are in agreement with the published pK$_d$ values for radiolabeled S1P binding to these receptors (12-14). The radioligand binding assay also revealed an excellent correlation between the pK$_i$ and the pK$_b$ for VPC23019 generated from the Schild analysis at both the S1P$_1$ and S1P$_3$ receptors, i.e. pK$_i$ values of 7.86 and 5.93, respectively (FIG. 4B and Table 2). Finally, VPC23019 was also found to be devoid of agonist activity at the S1P$_2$ receptor and radioligand binding studies with the S1P$_2$ receptor revealed that VPC23019 did not influence the binding of [$^{32}$P]S1P to the S1P$_2$ receptor at concentrations up to 10 μM (data not shown).

The pIC$_{50}$ values are the −log of the molar concentration of compound resulting in 50% of maximal inhibition of [$^{32}$P]S1P binding. The pK$_i$ values are the −log of the inhibitory binding constant (K$_i$), which were predicted using the Chang-Prusoff equation (K$_i$=IC$_{50}$/(1+[L]/K$_b$). In applying this equation, the concentration of radioligand (L) is 0.05 nM and the K$_b$ value used was that reported for the S1P-S1P$_1$ receptor interaction, i.e. 8.1 nM (12). The binding constants (pK$_b$) were calculated from the modified Schild analysis of Lew and Angus (9). The pK$_i$ and pK$_b$ values are reported as pK$_i$±S.E.M. and pK$_b$±S.E.M., respectively.

TABLE 2

Antagonist affinity at the S1P$_1$ and S1P$_3$ receptors

| Compound | Alkyl Chain | Ring Substitutions | pK$_i$ S1P$_1$ | pK$_i$ S1P$_3$ | pK$_b$ S1P$_1$ | pK$_b$ S1P$_3$ |
|---|---|---|---|---|---|---|
| VPC23019 | 8 | meta | 7.86 ± 0.16 | 5.93 ± 0.19 | 7.49 ± 0.15 | 5.98 ± 0.08 |
| WC25239 | 7 | meta | 7.87 ± 0.04 | 7.01 ± 0.14 | *6.25 ± 0.23 | 5.85 ± 0.10 |
| VPC23031 | 6 | meta | 7.21 ± 0.07 | 2.56 ± 13.4 | 6.87 ± 0.15 | *4.98 ± 0.62 |
| VPC23089 | 8 | ortho | 6.05 ± 0.16 | 5.80 ± 0.16 | 6.31 ± 0.23 | *6.36 |± 0.67 |

*Based on Schild analysis, the antagonism observed was not competitive

Example 11

The following illustrate representative pharmaceutical dosage forms, containing a compound of formula I (e.g., Compound VPC44116), for therapeutic or prophylactic use in humans.

| (i) Tablet 1 | mg/tablet |
|---|---|
| Compound VPC44116 | 100.0 |
| Lactose | 77.5 |
| Povidone | 15.0 |
| HO-propyl beta-cyclodextrin | 6.0-10.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound VPC44116 | 20.0 |
| Microcrystalline cellulose | 410.0 |
| HO-propyl beta-cyclodextrin | 6.0-10.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound VPC44116 | 10.0 |
| Colloidal silicon dioxide | 1.5 |
| HO-propyl beta-cyclodextrin | 6.0-10.0 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound VPC44116 (free acid form) | 1.0 |
| HO-propyl beta-cyclodextrin | 6.0-10.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
| --- | --- |
| Compound VPC44116 (free acid form) | 10.0 |
| Monobasic sodium phosphate | 0.3 |
| Dibasic sodium phosphate | 1.1 |
| HO-propyl beta-cyclodextrin | 6.0-10.0 |
| HO-propyl beta-cyclodextrin | 6.0-10.0 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
| --- | --- |
| Compound VPC44116 | 20.0 |
| Oleic acid | 10.0 |
| HO-propyl beta-cyclodextrin | 6.0-10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

BIBLIOGRAPHY

1. Brinkmann, V., Davis, M. D., Heise, C. E., Albert, R., Cottens, S., H of, R., Bruns, C., Prieschl, E., Baumruker, T., Hiestand, P., Foster, C. A., Zollinger, M., and Lynch, K. R. (2002) *J Biol Chem* 19, 21453-21457
2. Mandala, S., Hajdu, R., Beigstrom, J., Quackenbush, E., Xie, J., Milligan, J., Thornton, R., Shei, G. J., Card, D., Keohane, C, Rosenbach, M., Hale, J., Lynch, C. L., Rupprecht, K., Parsons, W., and Rosen, H. (2002) *Science* 296, 346-349.
3. Matloubian, M., Lo, C. G., Cinamon, G., Lesneski, M. J., Xu, Y., Brinkmann, V., Allende, M. L., Proia, R. L., and Cyster, J. G. (2004) *Nature* 427, 355-360
4. Sanna, M. G., Liao, J., Jo, E., Alfonso, C., Ahn, M. Y., Peterson, M. S., Webb, B., Lefebvre, S., Chun, J., Gray, N., and Rosen, H. (2004) *J Biol Chem* 279, 13839-13848
5. Kimura, T., Sato, K., Malchinkhuu, E., Tomura, H., Tamama, K., Kuwabara, A., Murakami, M., and Okajima, F. (2003) *Arterioscler Thromb Vase Biol* 23, 1283-1288
6. Jones, L., Schumm, J. S., and Tour, J. M. (1997) *J Org Chem* 62, 1388-1410
7. Zhang, T., Nanney, L. B., Luongo, C, Lamps, L., Heppner, K. J., DuBois, R. N., and Beauchamp, R. D. (1997) *Cancer Res* 57, 169-175
8. Im, D. S., Heise, C. E., Ancellin, N., O'Dowd, B. F., Shei, G. J., Heavens, R. P., Rigby, M. R., Hla, T., Mandala, S., McAllister, G., George, S. R., and Lynch, K. R. (2000) *J Biol Chem* 275, 14281-14286
9. Lew, M. J., and Angus, J. A. (1995) *Trends Pharmacol Sci* 16, 328-337
10. Clair, T., Aoki, J., Koh, E., Bandle, R. W., Nam, S. W., Ptaszynska, M. M., Mills, G. B., Schiffmann, E., Liotta, L. A., and Stracke, M. L. (2003) *Cancer Res* 63, 5446-545.3
11. Clemens, J. J., Davis, M. D., Lynch, K. R., and Macdonald, T. L. (2003) *Bioorg Med Chem Lett* 13, 3401-3404
12. Lee, M. J., Van Brooklyn, J. R., Thangada, S., Liu, C. H., Hand, A. R., Menzeleev, R., Spiegel, S., and Hla, T. (1998) *Science* 279, 1552-1555
13. Van Brocklyn, J. R., Tu, Z., Edsall, L. C., Schmidt, R. R., and Spiegel, S. (1999) *J Biol Chem* 274, 4626-4632
14. Kon, J., Sato, K., Watanabe, T., Tomura, H., Kuwabara, A., Kimura, T., Tamama, K., Ishizuka, T., Murata, N., Kanda, T., Kobayashi, I., Ohta, H., Ui, M., and Okajima, F. (1999) *J Biol Chem* 274, 23940-23947
15. Kiuchi, M., Adachi, K., Kohara, T., Minoguchi, M., Hanano, T., Aoki, Y., Mishina, T., Arita, M., Nakao, N., Ohtsuki, M., Hoshino, Y., Teshima, K., Chiba, K., Sasaki, S., and Fujita, T. (2000) *J Med Chem* 43, 2946-2961
16. Yanagawa, Y., Hoshino, Y., and Chiba, K. (2000) *Int J Immunopharmacol* 22, 597-602
17. Chiba, K., Yanagawa, Y., Masubuchi, Y., Kataoka, H., Kawaguchi, T., Ohtsuki, M., and Hoshino, Y. (1998) *J Immunol* 160, 5037-5044
18. Hoshino, Y., Yanagawa, Y., Ohtsuki, M., Nakayama, S., Hashimoto, T., and Chiba, K. (1999) *Transplant Proc* 31, 1224-1226
19. Yanagawa, Y., Hoshino, Y., Kataoka, H., Kawaguchi, T., Ohtsuki, M., Sugahara, K., and Chiba, K. (1999) *Transplant Proc* 31, 1227-1229
20. Brinkmann, V., Pinschewer, D. D., Feng, L., and Chen, S. (2001) *Transplantation* 72, 764-769
21. Suzuki, S., Enosawa, S., Kakefuda, T., Li, X. K., Mitsusada, M., Takahara, S., and Amemiya, H. (1996) *Transpl Immunol* 4, 252-255
22. Xie, J. H., Nomura, N., Koprak, S. L., Quackenbush, E. J., Forrest, M. J., and Rosen, H. (2003) *J Immunol* 170, 3662-3670
23. Fujino, M., Funeshima, N., Kitazawa, Y., Kimura, H., Amemiya, H., Suzuki, S., and Li, X. K. (2003) *J Pharmacol Exp Ther* 305, 70-77
24. Yang, Z., Chen, M., Fialkow, L. B., Ellett, J. D., Wu, R., Brinkmann, V., Nadler, J. L., and Lynch, K. R. (2003) *Clin Immunol* 107, 30-35
25. Maki, T., Gottschalk, R., and Monaco, A. P. (2002) *Transplantation* 74, 1684-1686
26. Sanchez, T., Estrada-Hernandez, T., Paik, J. H., Wu, M. T., Venkataraman, K., Brinkmann, V., Claffey, K., and Hla, T. (2003) *J Biol Chem* 278, 47281-47290
27. Hale, J. J., Doherty, G., Toth, L., Mills, S. G., Hajdu, R., Ann Keohane, C., Rosenbach, M., Milligan, J., Shei, G. J., Chrebet, G., Bergstrom, J., Card, D., Forrest, M., Sun, S. Y., West, S., Xie, H., Nomura, N., Rosen, H., and Mandala, S. (2004) *Bioorg Med Chem Lett* 14, 3501-3505
28. Hale, J. J., Doherty, G., Toth, L., Li, Z., Mills, S. G., Hajdu, R., Ann Keohane, C., Rosenbach, M., Milligan, J., Shei, G. J., Chrebet, G., Bergstrom, J., Card, D., Rosen, H., and Mandala, S. (2004) *Bioorg Med Chem Lett* 14, 3495-3499
29. Forrest, M., Sun, S. Y., Hajdu, R., Bergstrom, J., Card, D., Doherty, G., Hale, J., Keohane, C., Meyers, C., Milligan, J., Mills, S., Nomura, N., Rosen, H., Rosenbach, M., Shei, G. J., Singer, I I, Tian, M., West, S., White, V., Xie, J., Proia, R. L., and Mandala, S. (2004) *J Pharmacol Exp Ther* 309, 758-768
30. Graler, M. H., and Goetzl, E. J. (2004) *FASEB* 18, 551-553
31. Davis, M. D., Clemens, J. J., MacDonald, T L., and Lynch, K. R., (2005) *J Biol Chem* 280, 9833-9841.

The abbreviations used herein have their conventional meaning within the chemical and biological arts. All publications, patents, and patent documents cited in the specification are incorporated by reference herein, as though individually incorporated by reference, hi the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention.

What is claimed is:

1. A compound having formula (I):

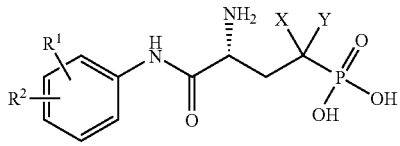

wherein X and Y taken together with the atom to which they are attached form a keto group;
R¹ is hydrogen, halo, tri-fluoromethyl, ($C_1$-$C_6$)-alkyl, ($C_1$-$C_6$) alkyl substituted with halo, hydroxy, alkoxy, or cyano;
R² is ($C_1$-$C_{10}$)alkyl, ($C_3$-$C_8$)-cycloalkyl substituted alkyl, ($C_2$-$C_6$)alkenyl, ($C_2$-$C_6$)alkynyl, aryl, alkyl substituted aryl, arylalkyl or aryl substituted arylalkyl; or a pharmaceutically acceptable ester or salt thereof.

2. The compound of claim 1 wherein $R_2$ is ortho or meta to the amide.

3. The compound of claim 1 wherein $R_2$ is meta to the amide.

4. The compound of claim 1 wherein the $R^2$ alkyl groups have from 5-8 carbon atoms.

5. The compound of claim 1 having the formula:

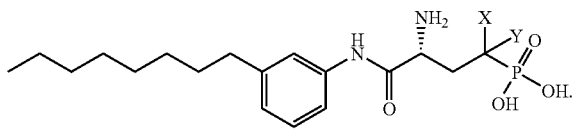

6. The compound of claim 1 in the form of a pharmaceutically acceptable salt of a compound of formula 1.

7. The compound of claim 1 in the form of a pharmaceutically acceptable ester of a compound of formula 1.

8. The compound of claim 7 wherein the ester group is methyl, ethyl, propyl, benzyl, or has the formula

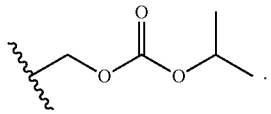

9. A pharmaceutical composition comprising a compound of claim 1, having formula (I):

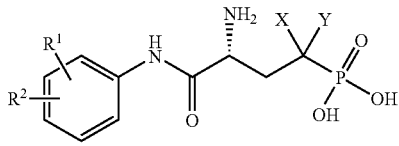

wherein X and Y taken together with the atom to which they are attached form a keto group;
R¹ is hydrogen, halo, tri-fluoromethyl, ($C_1$-$C_6$)-alkyl, ($C_1$-$C_6$) alkyl substituted with halo, hydroxy, alkoxy, or cyano;
R² is ($C_1$-$C_{10}$)alkyl, ($C_3$-$C_8$)-cycloalkyl substituted alkyl, ($C_2$-$C_6$)alkenyl, ($C_2$-$C_6$)alkynyl, aryl, alkyl substituted aryl, arylalkyl or aryl substituted arylalkyl; or a pharmaceutically acceptable ester or salt thereof; and
a pharmaceutically acceptable carrier.

10. A kit for administering at least one compound of claim 1 having formula (I):

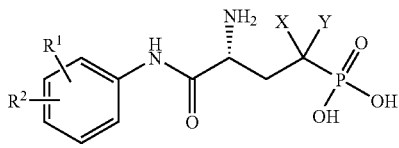

wherein X and Y taken together with the atom to which they are attached form a keto group;
R¹ is hydrogen, halo, tri-fluoromethyl, ($C_1$-$C_6$)-alkyl, ($C_1$-$C_6$) alkyl substituted with halo, hydroxy, alkoxy, or cyano;
R² is ($C_1$-$C_{10}$)alkyl, ($C_3$-$C_8$)-cycloalkyl substituted alkyl, ($C_2$-$C_6$)alkenyl, ($C_2$-$C_6$)alkynyl, aryl, alkyl substituted aryl, arylalkyl or aryl substituted arylalkyl; or a pharmaceutically acceptable ester or salt thereof;
to a patient in need thereof, said kit comprising a pharmaceutical composition comprising at least one compound having formula (I), an applicator, and instructional material for the use thereof.

* * * * *

UNITED STATES PATENT AND TRADEMARK OFFICE
CERTIFICATE OF CORRECTION

PATENT NO. : 7,888,527 B2
APPLICATION NO. : 11/720998
DATED : February 15, 2011
INVENTOR(S) : Lynch et al.

It is certified that error appears in the above-identified patent and that said Letters Patent is hereby corrected as shown below:

Government Funding

In column 1, line 17-20, delete "The invention described herein was made with government support under Grant Numbers GM067958 and GM064101, awarded by the National Institutes of Health. The United States Government" and insert --This invention was made with government support under GM067958 and GM064101 awarded by the National Institutes of Health. The government--, therefor Signed and Sealed this
Seventh Day of June, 2016

Michelle K. Lee
*Director of the United States Patent and Trademark Office*